United States Patent
Miyata et al.

(10) Patent No.: US 9,870,404 B2
(45) Date of Patent: Jan. 16, 2018

(54) COMPUTER SYSTEM, DATA MANAGEMENT METHOD, AND RECORDING MEDIUM STORING PROGRAM

(75) Inventors: Yasushi Miyata, Tokyo (JP); Shoji Kodama, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 406 days.

(21) Appl. No.: 14/399,065

(22) PCT Filed: Sep. 7, 2012

(86) PCT No.: PCT/JP2012/072838
§ 371 (c)(1),
(2), (4) Date: Nov. 24, 2014

(87) PCT Pub. No.: WO2014/038057
PCT Pub. Date: Mar. 13, 2014

(65) Prior Publication Data
US 2015/0106363 A1 Apr. 16, 2015

(51) Int. Cl.
*G06F 7/00* (2006.01)
*G06F 17/30* (2006.01)
(Continued)

(52) U.S. Cl.
CPC .......... *G06F 17/3053* (2013.01); *G06F 11/00* (2013.01); *G06F 11/006* (2013.01);
(Continued)

(58) Field of Classification Search
CPC ...... G06Q 10/00; G06Q 50/24; G06F 11/006; G06F 2201/182; G06F 11/3476; G06F 11/00; G06F 12/00; G06F 17/3053
See application file for complete search history.

(56) References Cited

U.S. PATENT DOCUMENTS 3,564,226 A * 2/1971 Seligman .................. G06F 7/57
708/490
3,566,093 A * 2/1971 Joyce .................. G06F 11/1032
714/805

(Continued)

FOREIGN PATENT DOCUMENTS

JP 2001-325533 A 11/2001
JP 2007-282026 A 10/2007

(Continued)

*Primary Examiner* — Daniel Kuddus
(74) *Attorney, Agent, or Firm* — Mattingly & Malur, PC

(57) ABSTRACT

When plural processing programs for generating post-processing data which is a source of services to be provided are present, a relationship between post-processing data and a data group which is a source of the post-processing data is managed. The processing units acquire pre-processing data, execute given processing, and generate post-processing data as a result of the processing. At an opportunity to acquire the pre-processing data, a process ID indicative of ordering of the acquisition, and not updated before and after the given processing is allocated to acquired pre-processing data. The generated post-processing data is stored, and in extracting the post-processing data satisfying the given data search condition, the post-processing data having a process ID equal to or before the process ID that is latest in the post-processing data and oldest among the respective processing units is extracted from the post-processing data that satisfies the data search condition.

13 Claims, 22 Drawing Sheets

(51) Int. Cl.
*G06F 12/00* (2006.01)
*G06F 11/00* (2006.01)
*G06F 11/34* (2006.01)
*G06Q 10/00* (2012.01)
*G06Q 50/24* (2012.01)

(52) U.S. Cl.
CPC .......... *G06F 11/3476* (2013.01); *G06F 12/00* (2013.01); *G06Q 10/00* (2013.01); *G06F 2201/82* (2013.01); *G06Q 50/24* (2013.01)

(56) References Cited

U.S. PATENT DOCUMENTS

| | | | | |
|---|---|---|---|---|
| 5,600,826 | A * | 2/1997 | Ando | G06F 17/30961 |
| 5,764,451 | A * | 6/1998 | Katz | G11B 5/02 |
| | | | | 360/123.36 |
| 5,768,451 | A * | 6/1998 | Hisamitsu | G06K 9/723 |
| | | | | 382/309 |
| 7,076,486 | B2 * | 7/2006 | Livshits | G06F 17/2211 |
| 7,164,846 | B2 * | 1/2007 | Ohta | G06F 17/30802 |
| | | | | 348/E11.021 |
| 7,167,846 | B2 * | 1/2007 | Provost | G06N 5/003 |
| | | | | 706/6 |
| 7,386,439 | B1 * | 6/2008 | Charnock | G06F 17/30699 |
| | | | | 704/9 |
| 7,895,188 | B2 * | 2/2011 | Lee | G06F 17/30675 |
| | | | | 707/713 |
| 8,095,541 | B2 | 1/2012 | Uchida | |
| 8,823,833 | B2 * | 9/2014 | Koshikawa | H04N 5/772 |
| | | | | 348/231.3 |
| 2005/0131860 | A1 * | 6/2005 | Livshits | G06F 17/2211 |
| 2007/0150453 | A1 * | 6/2007 | Morita | G06F 17/30265 |
| 2007/0161453 | A1 * | 7/2007 | Iwasaki | F16H 3/66 |
| | | | | 475/280 |
| 2008/0040401 | A1 * | 2/2008 | Reinsch | G06F 8/68 |
| 2010/0202465 | A1 * | 8/2010 | Sakata | H04L 45/00 |
| | | | | 370/400 |
| 2010/0289925 | A1 * | 11/2010 | Koshikawa | H04N 5/772 |
| | | | | 348/239 |
| 2012/0030207 | A1 * | 2/2012 | Kim | H04W 4/185 |
| | | | | 707/740 |
| 2013/0318540 | A1 * | 11/2013 | Kumura | G06F 9/46 |
| | | | | 718/106 |

FOREIGN PATENT DOCUMENTS

| | | |
|---|---|---|
| JP | 2009-271919 A | 11/2009 |
| JP | 2010-102582 A | 5/2010 |
| JP | 4793067 B2 | 10/2011 |
| WO | 2012/105593 A1 | 8/2012 |

* cited by examiner

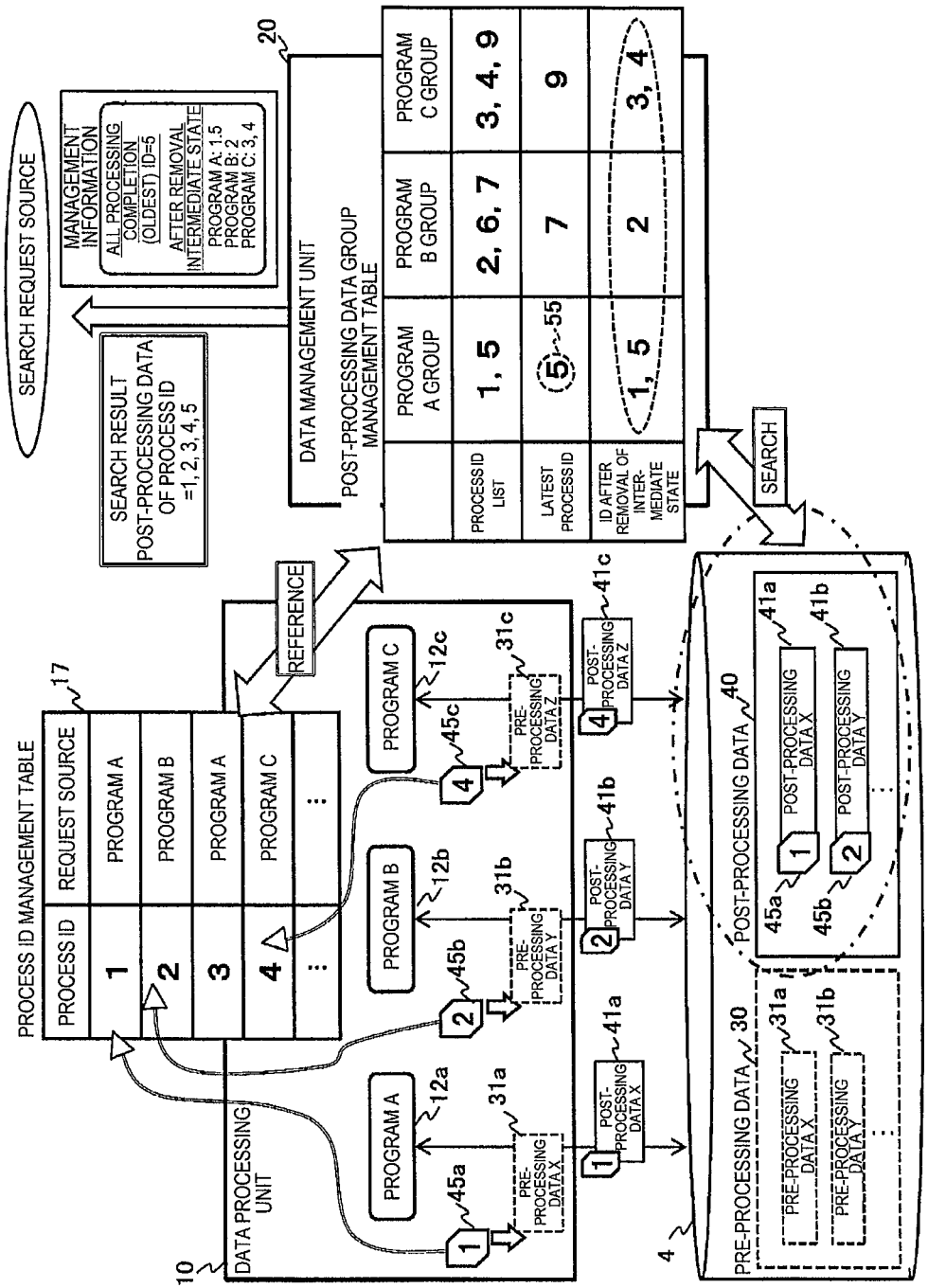
[FIG. 1]

[FIG. 2]
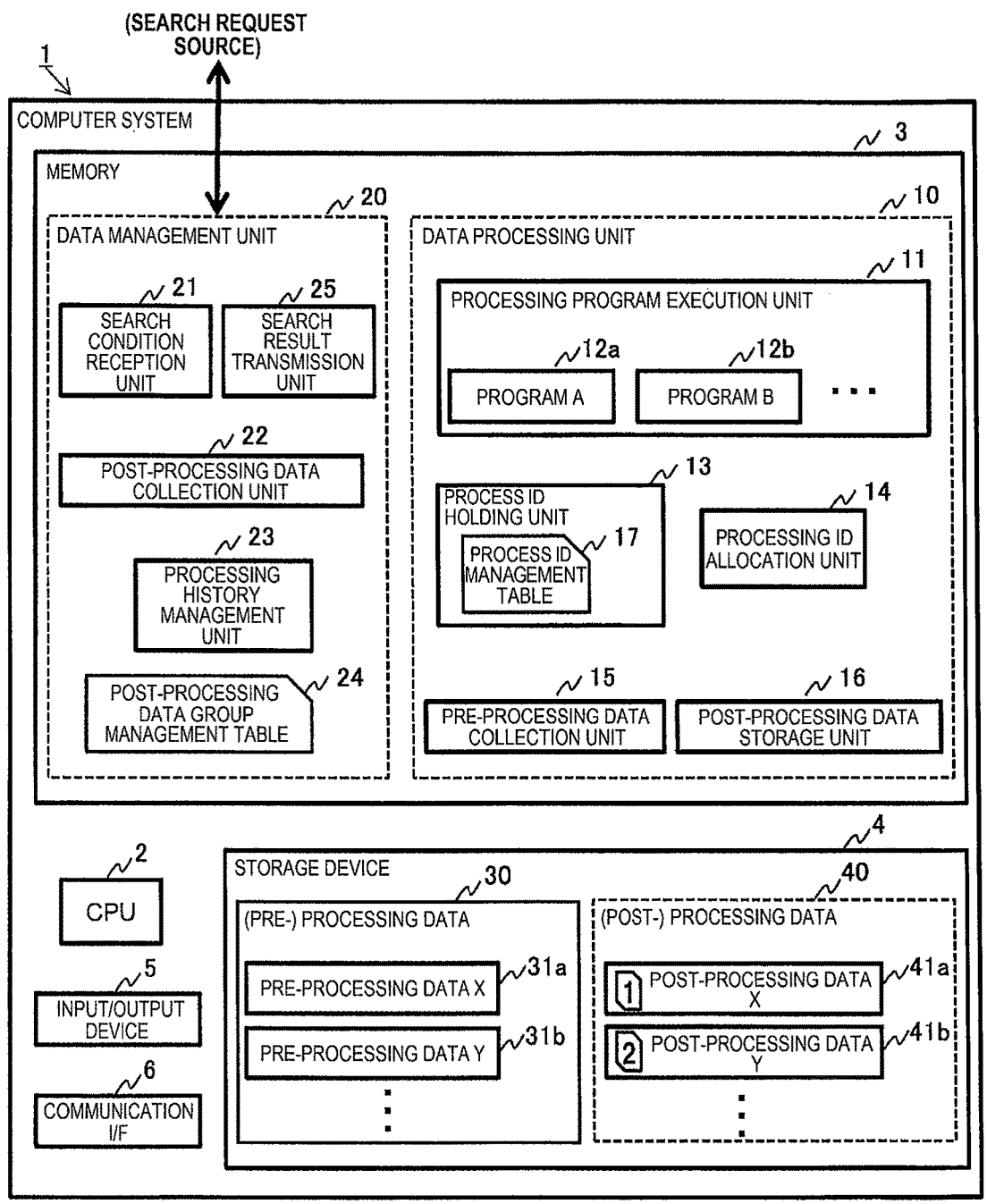

[FIG. 3]

| PROCESS ID | REQUEST SOURCE |
|---|---|
| 1 | PROGRAM A |
| 2 | PROGRAM B |
| 3 | PROGRAM A |
| ... | ... |

[FIG. 4]

|  | PROGRAM A GROUP | PROGRAM B GROUP | PROGRAM C GROUP |
|---|---|---|---|
| LATEST PROCESS ID | 5 | 7 | 9 |
| PROCESS ID LIST | 1, 5 | 2, 6, 7 | 3, 4, 9 |
| ID LIST AFTER REMOVAL OF INTERMEDIATE STATE | 1, 5 | 2 | 3, 4 |

[FIG. 5]

```
<Header>
ProcessID=1
<Body>
~~~
```

[FIG. 6]

```
<Data>
  <Source>~~~</Source>
  <Metadata>
    <ProcessID>1</ProcessID>  }~45
    ~~~
  </Metadata>
</Data>
```

[FIG. 7]
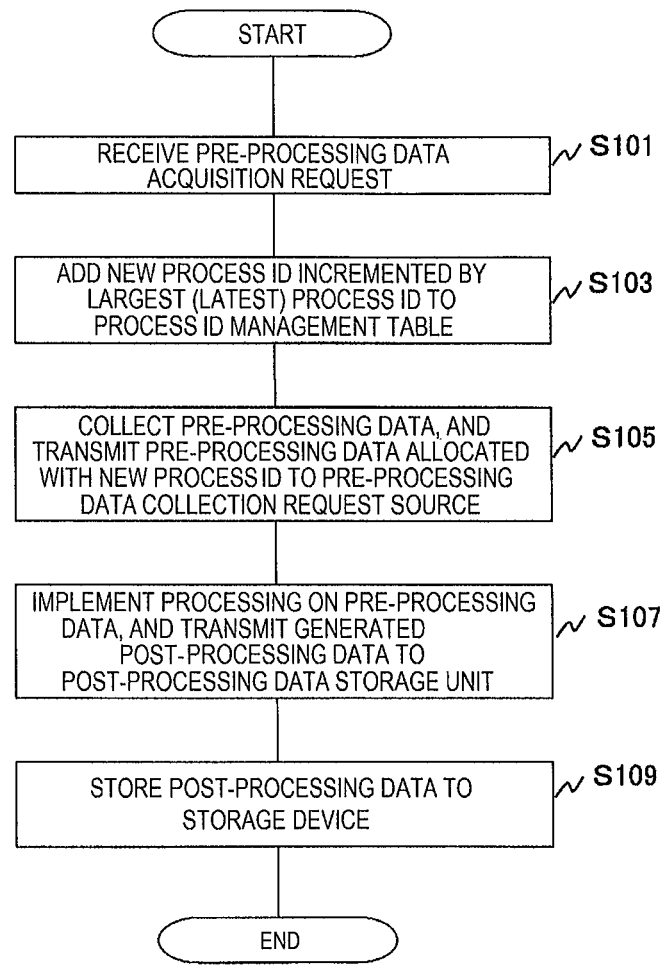

[FIG. 8]
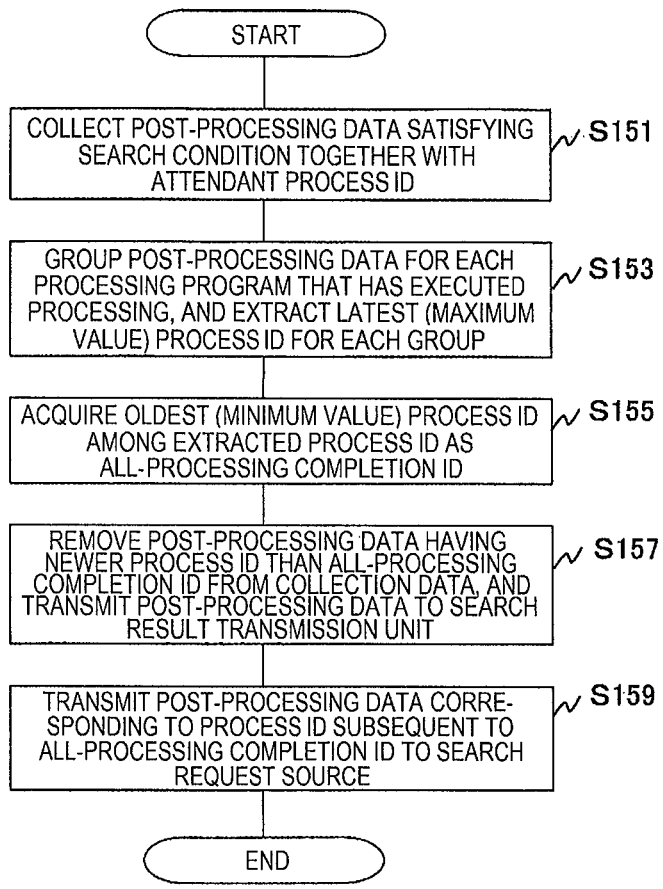
[FIG. 9]
| DEPENDENT GROUP ID | DEPENDENT PROCESSING |
|---|---|
| 1 | PROGRAM A, PROGRAM B |
| 2 | PROGRAM C, PROGRAM D |
| ... | ... |

[FIG. 10]
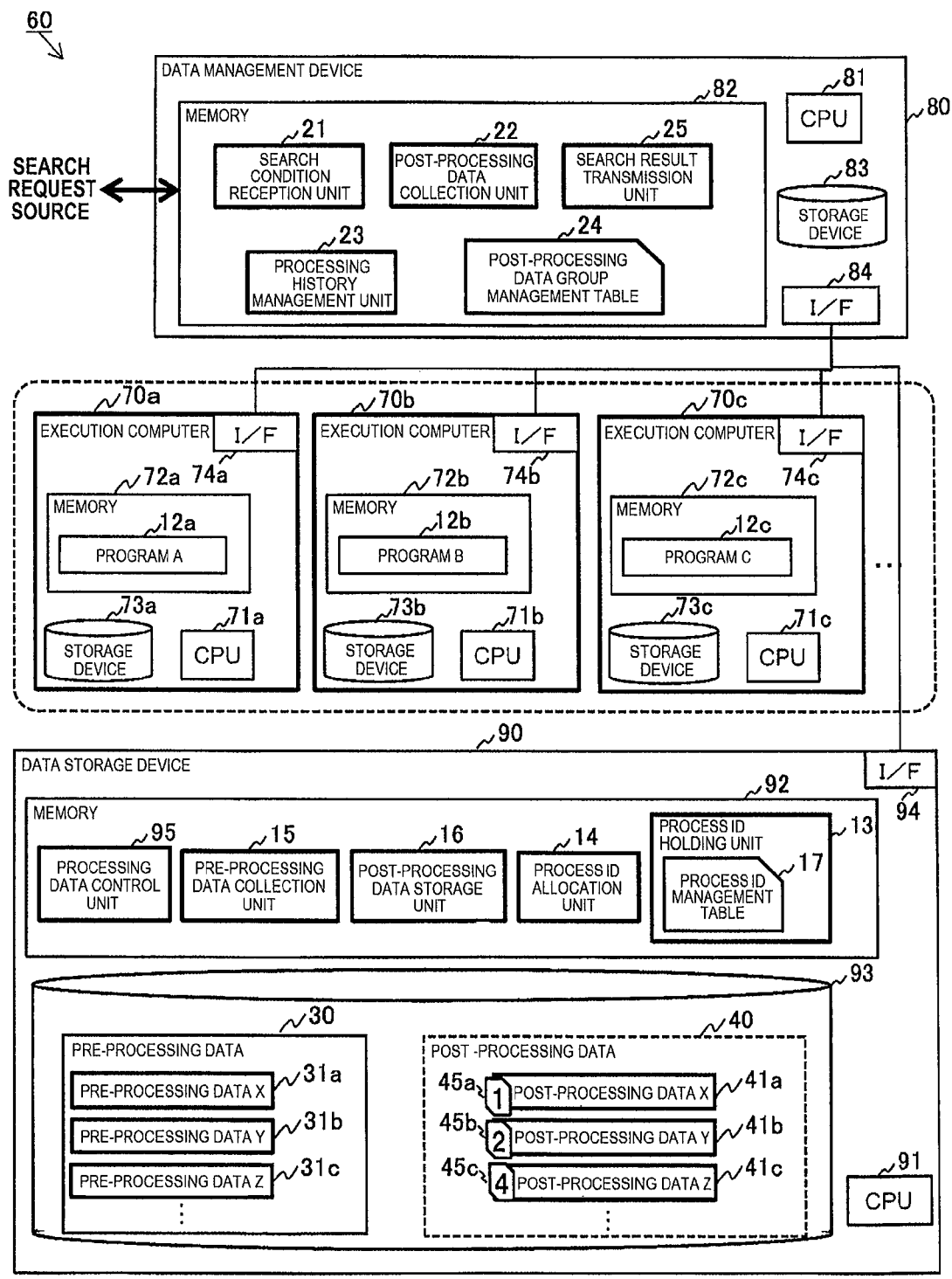

[FIG. 11]
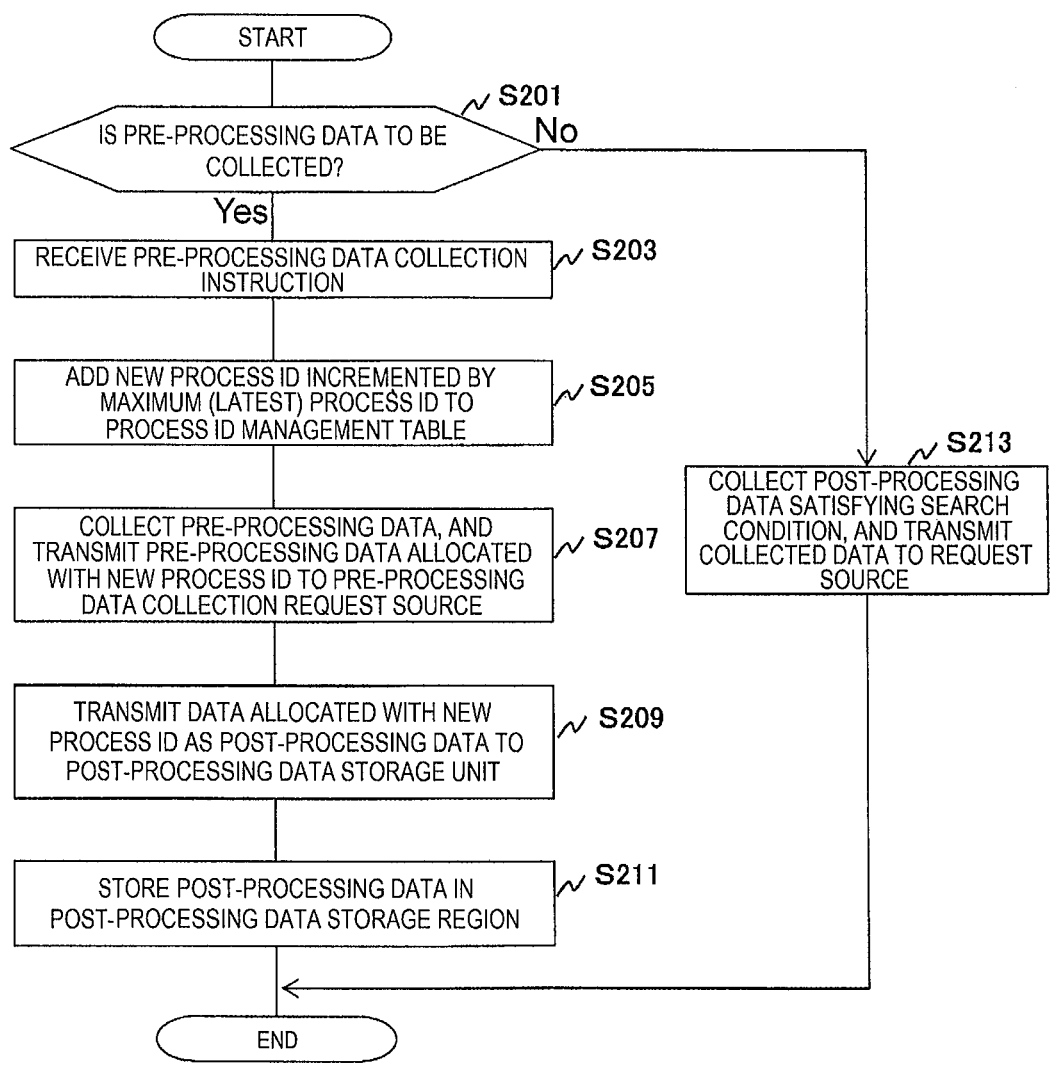

[FIG. 12]
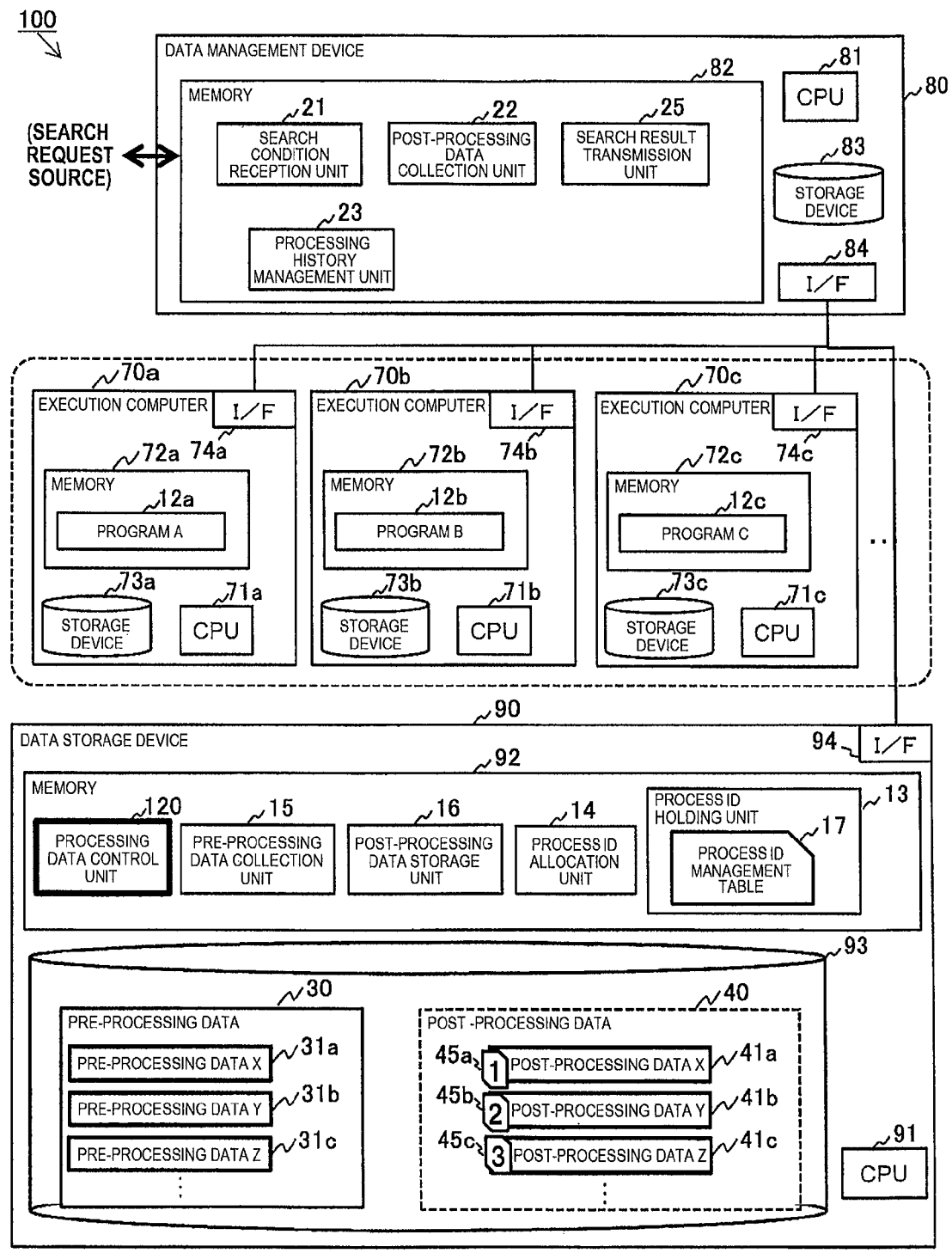

[FIG. 13]
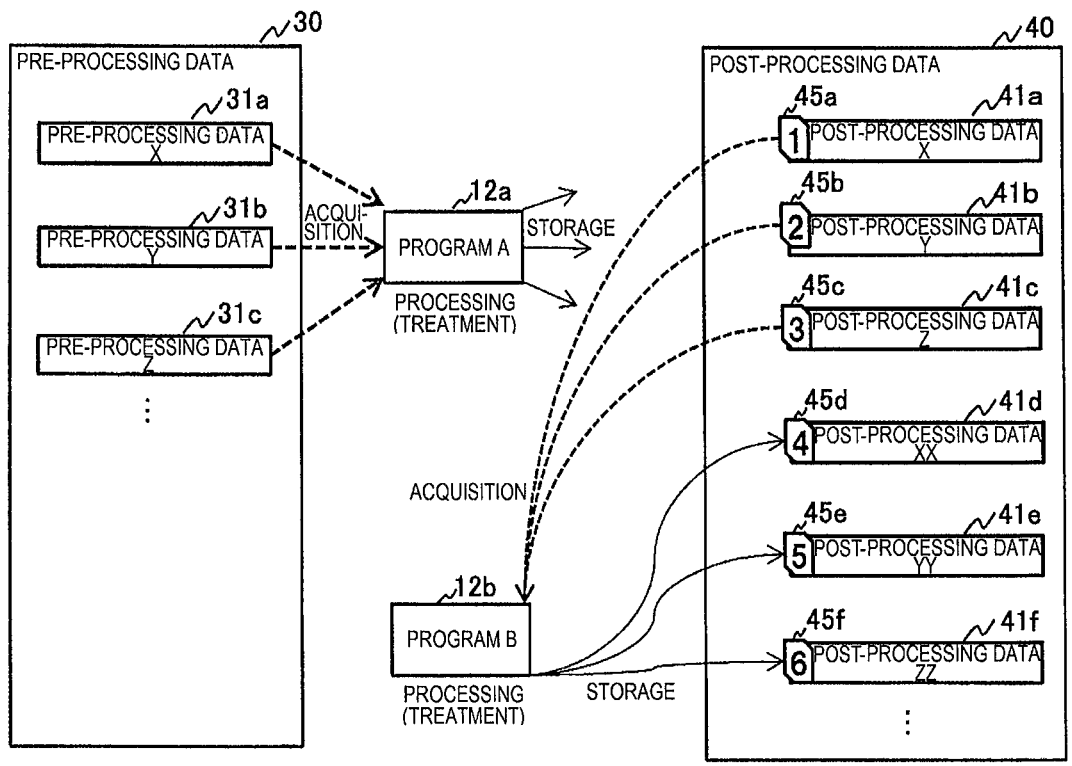
[FIG. 14]
| PROCESS ID | REQUEST SOURCE |
|---|---|
| 1 | PROGRAM A |
| 2 | PROGRAM A |
| 3 | PROGRAM A |
| 4 | PROGRAM B |
| 5 | PROGRAM B |
| 6 | PROGRAM B |

[FIG. 15A]

```
<Header>
ProcessID=1  ⎤
ProcessID=3  ⎦ ～ 45
<Body>
～～～
```

[FIG. 15B]

```
<Data>
  <Source>～～～</Source>
  <Metadata>
    <IDList>1, 3</IDList> ～ 45
    ～～～
  </Metadata>
</Data>
```

[FIG. 16]
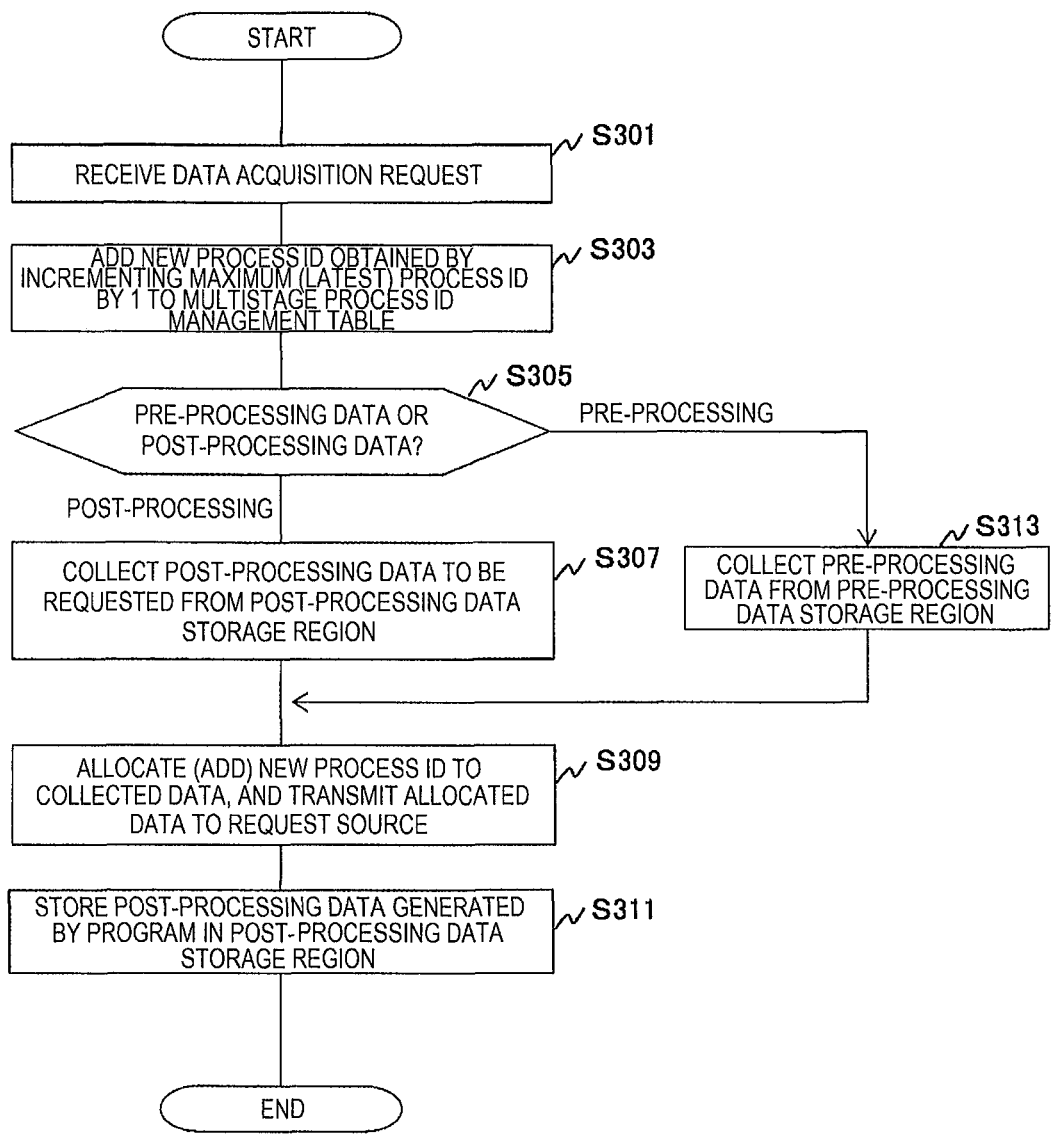

[FIG. 17]
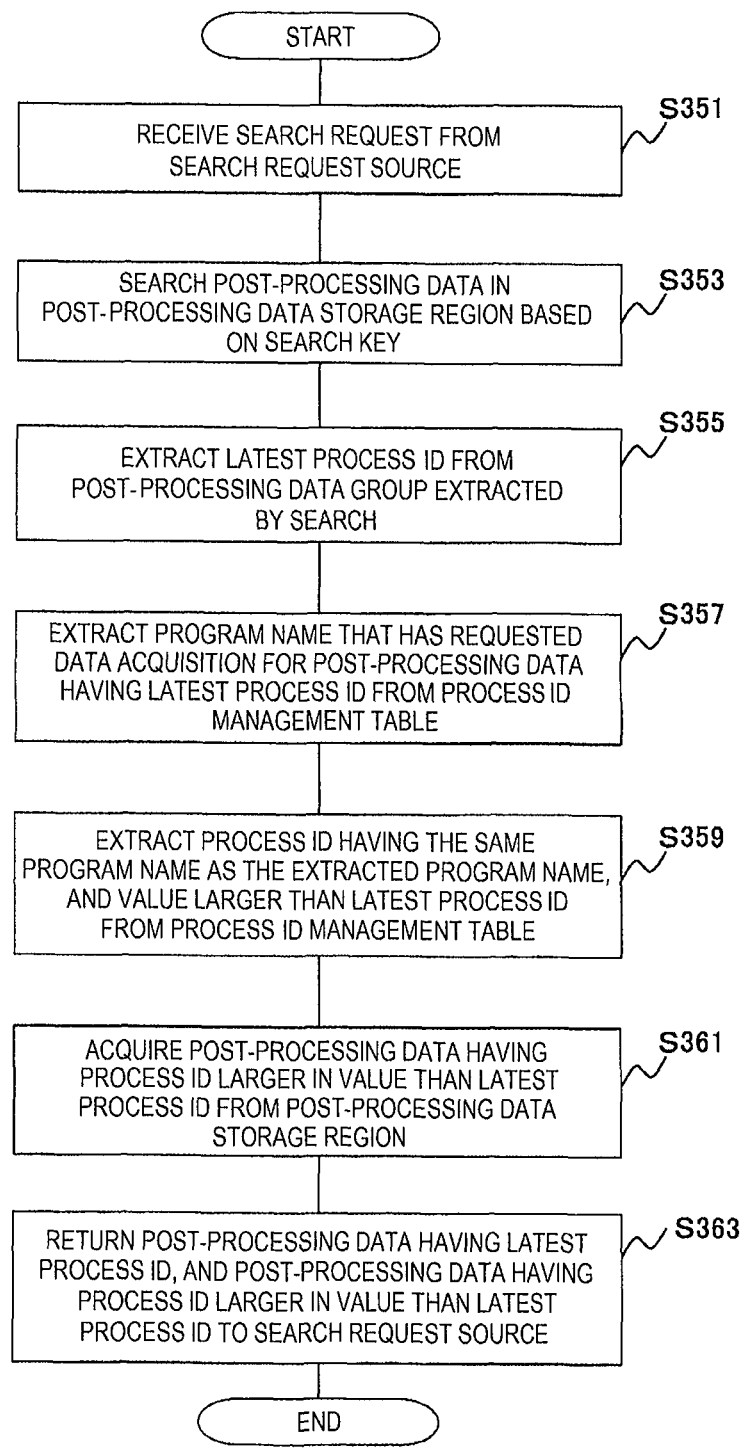

[FIG. 18]
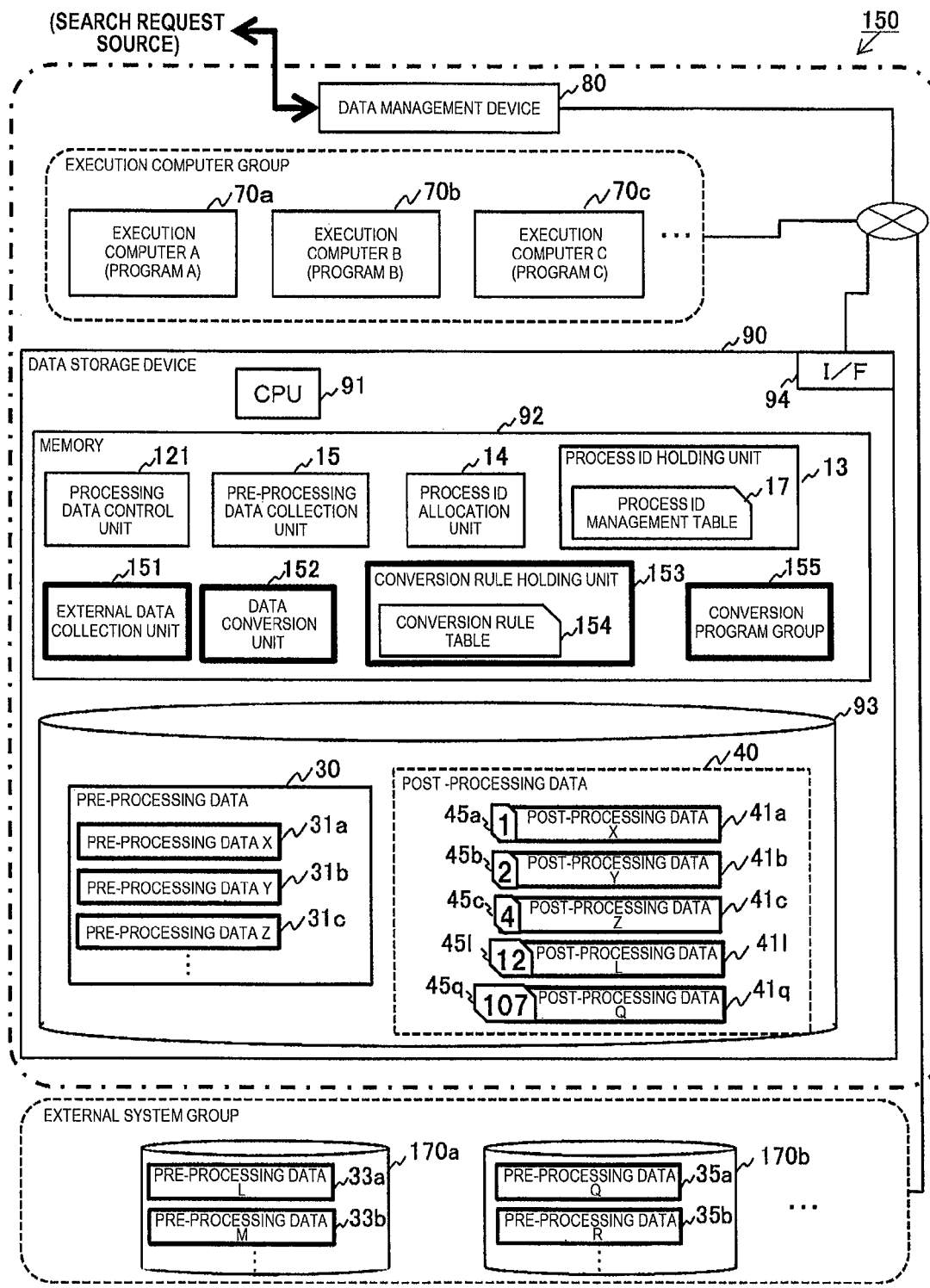

[FIG. 19]

| DATA FORMAT | CONVERSION PROGRAM |
|---|---|
| CHARACTER STRING | A CONVERSION PROGRAM |
| IMAGE | B CONVERSION PROGRAM |
| ... | ... |

[FIG. 20]
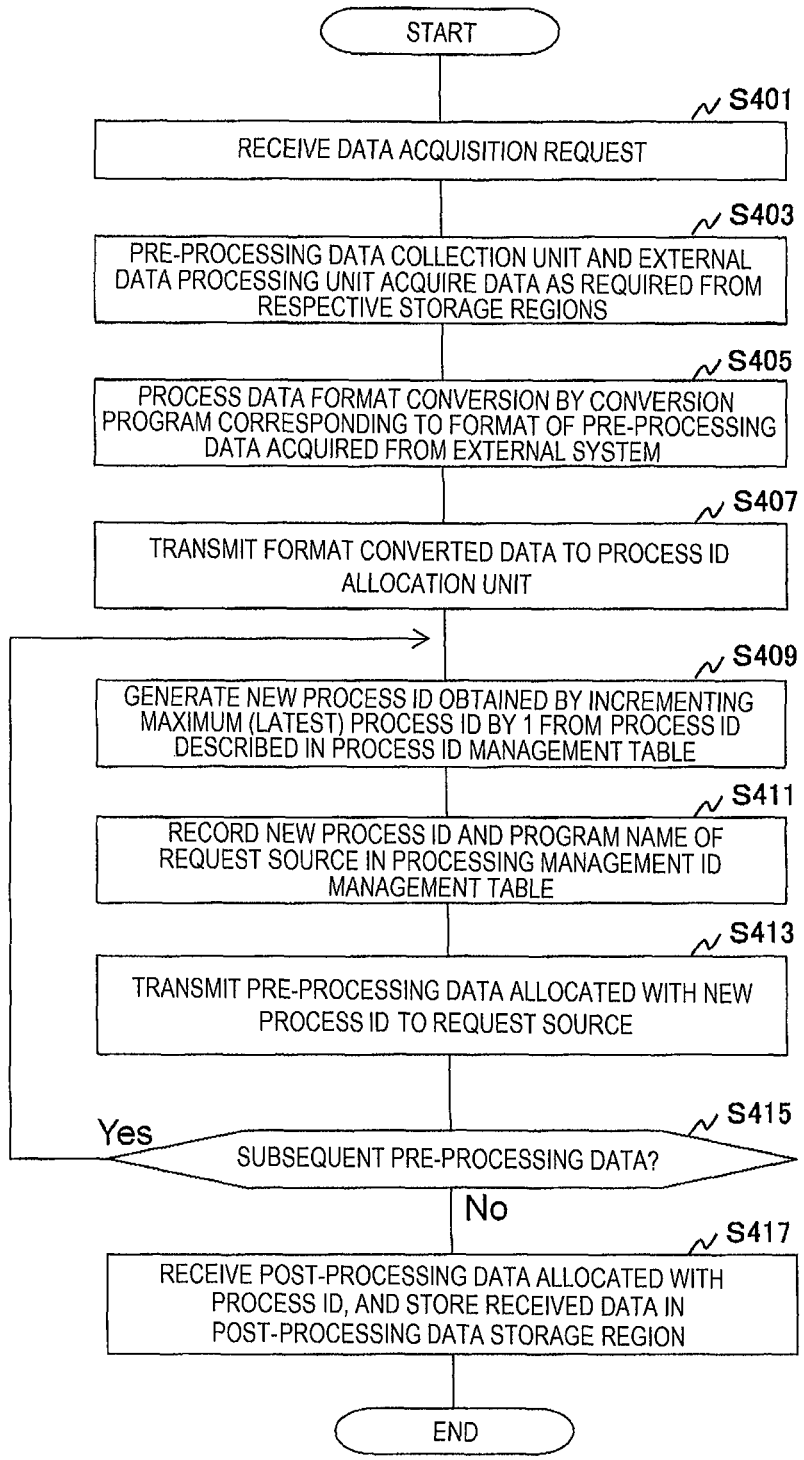

[FIG. 21]
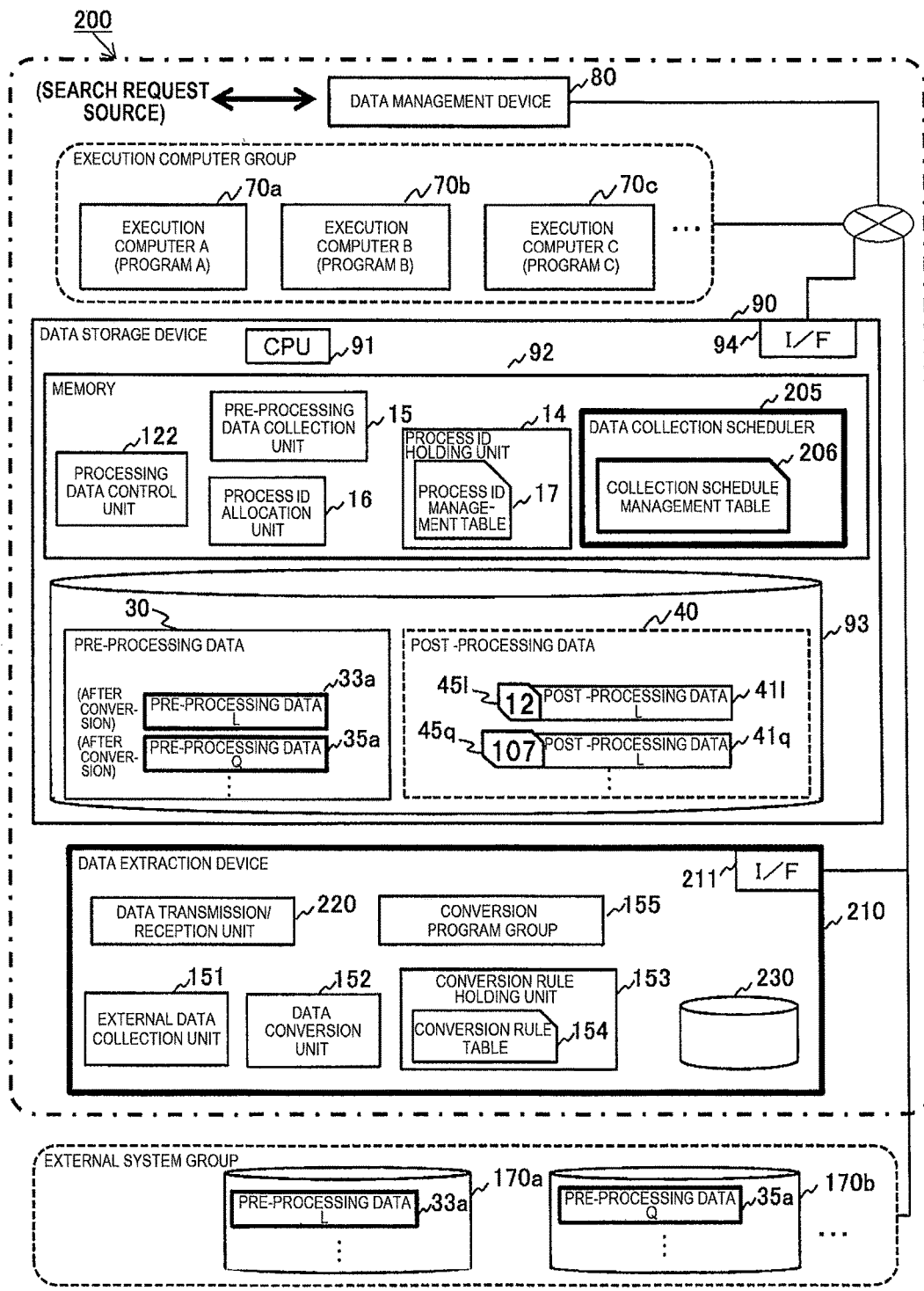

[FIG. 22]
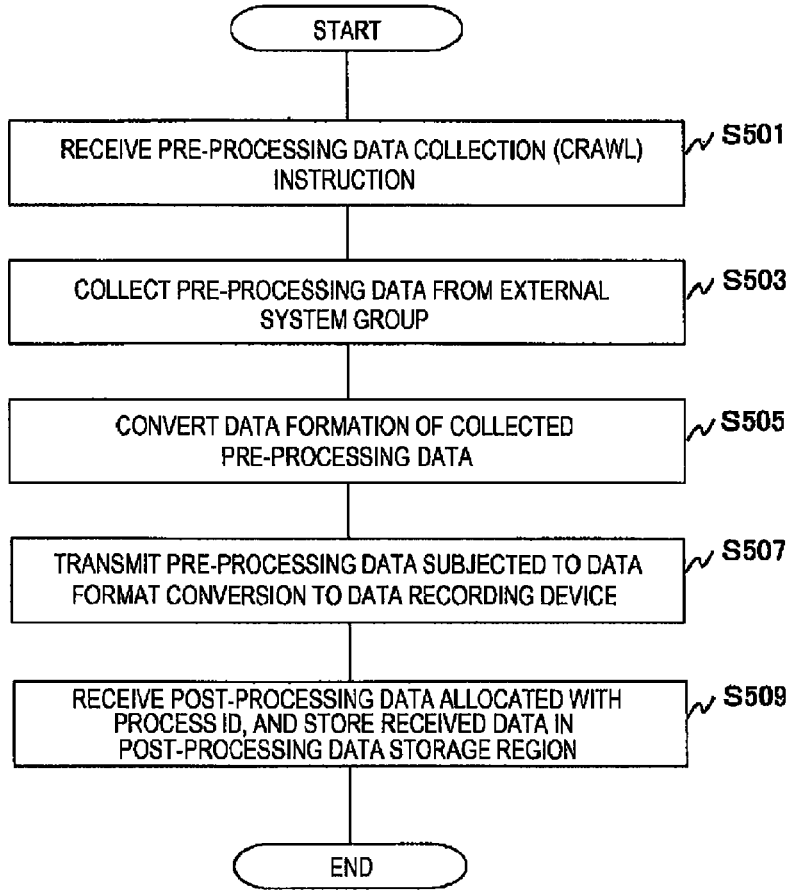
[FIG. 23]

[FIG. 24]
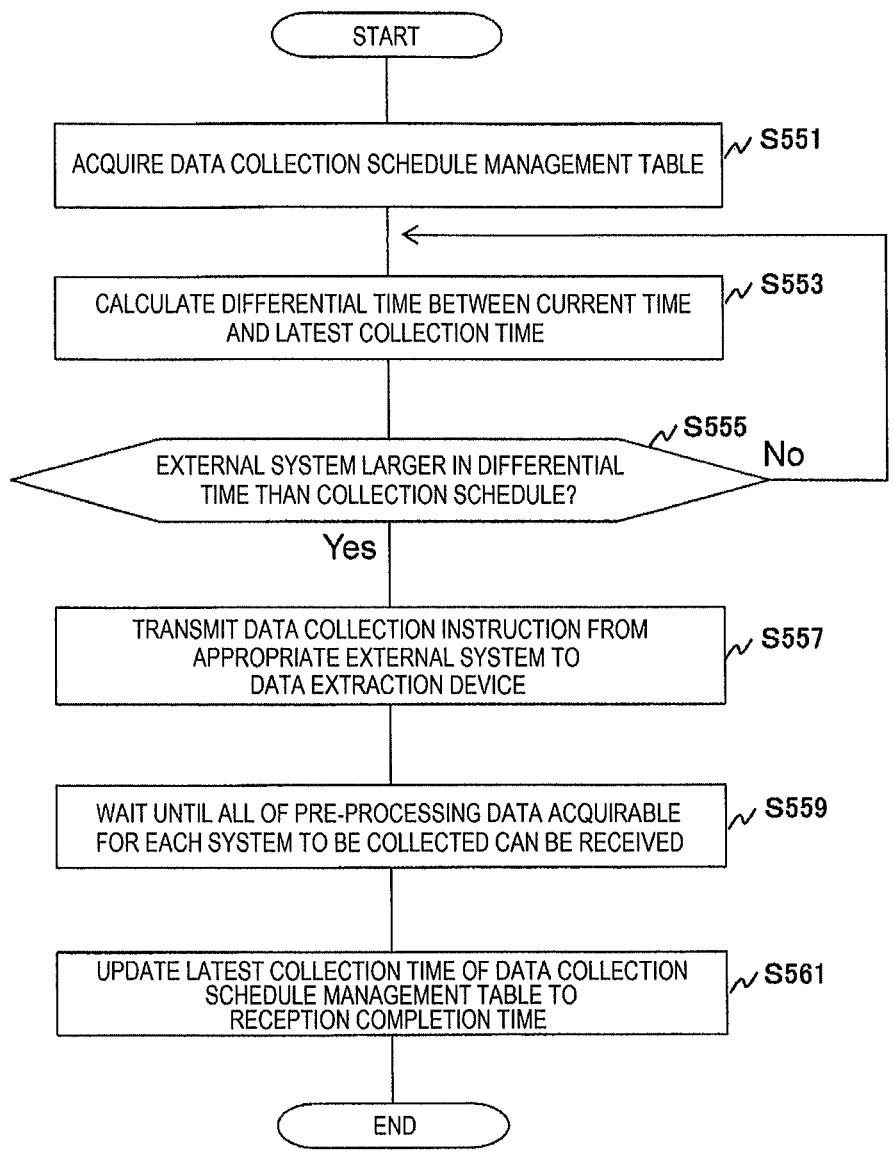

[FIG. 25]
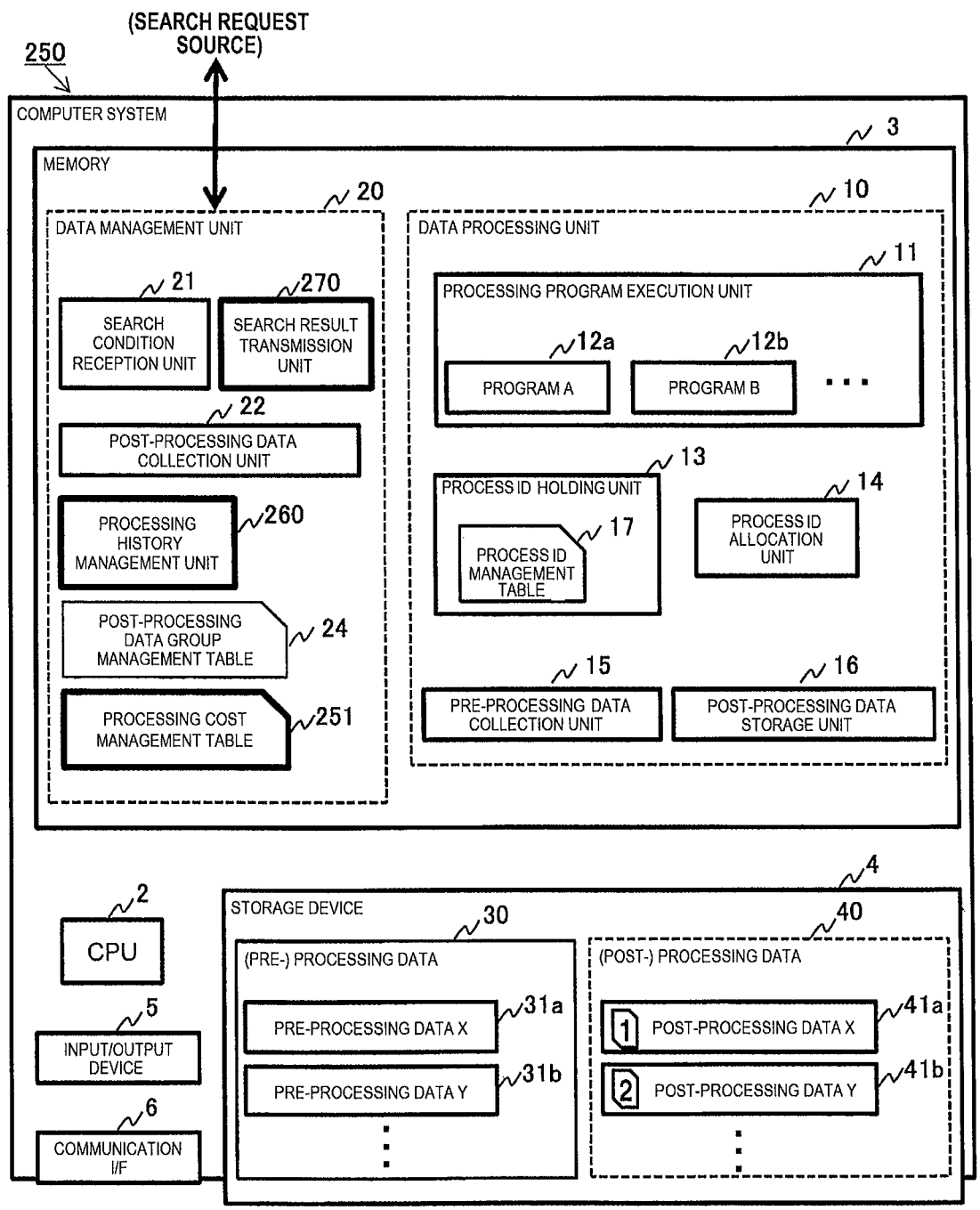

[FIG. 26]

| PROGRAM | POST-PROCESSING DATA PRICE |
|---|---|
| PROGRAM A | ¥100／1MB |
| PROGRAM B | Free |
| PROGRAM C | ¥1000／File |
| ... | ... |

DATA SEARCH http://example.com/search

SEARCH WORD : [STOCK PRICE, RISING, STOCKS] 305

FREE SEARCH RESULTS

APPLICABLE: 200 CASES

1. ～～～
2. ～～～
⋮

310

PAID SEARCH RESULTS

1. PROGRAM A RESULT
   APPLICABLE: 10 CASES
   PRICE: ¥1000

[PURCHASE] 331a

2. PROGRAM C RESULT
   APPLICABLE: 30 CASES
   PRICE: ¥30000

[PURCHASE] 331b
   ⋮

330

[FIG. 28]
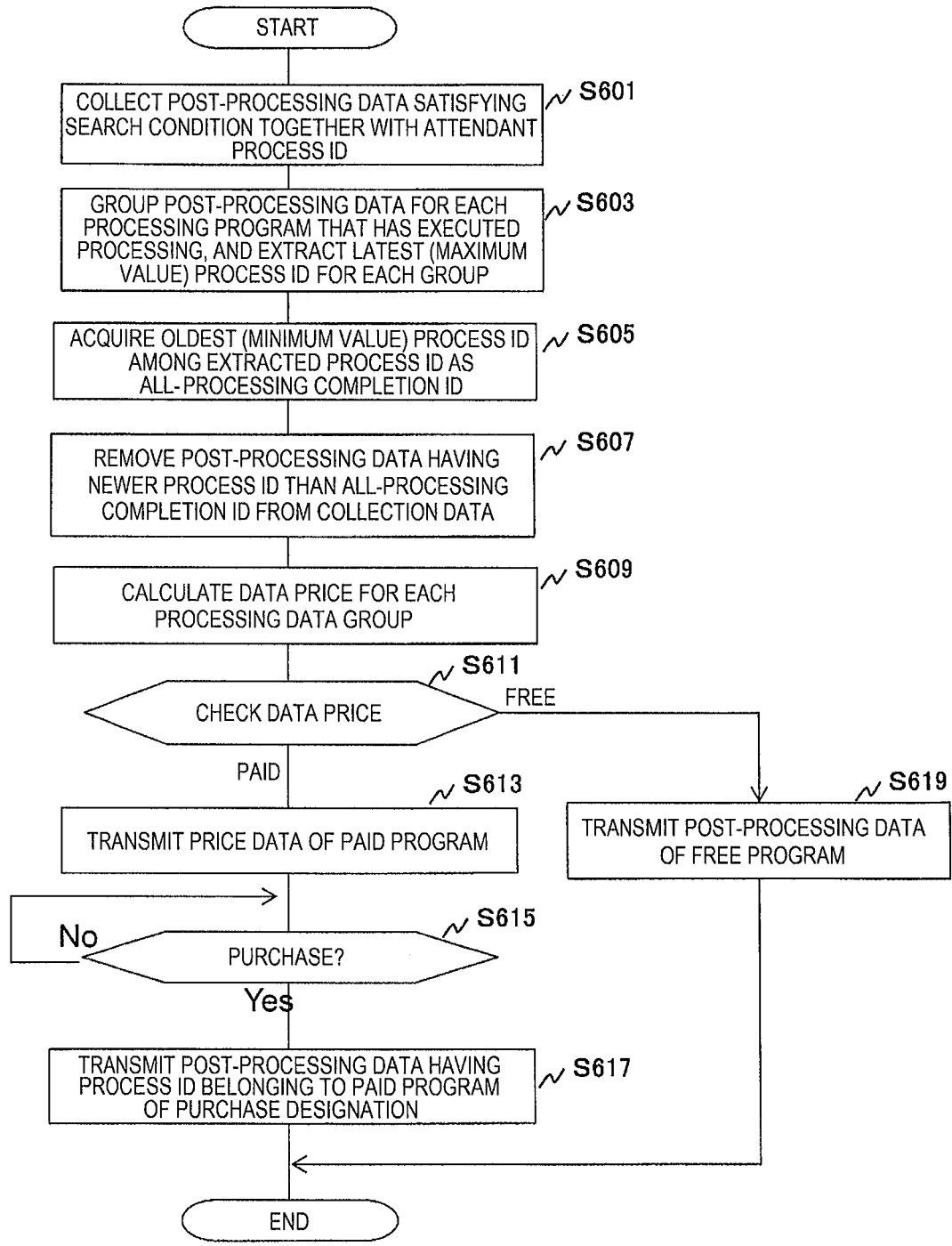

COMPUTER SYSTEM, DATA MANAGEMENT METHOD, AND RECORDING MEDIUM STORING PROGRAM

TECHNICAL FIELD

The present invention relates to a computer system, a data management method, and a recording medium storing a program, and more particularly to a computer system, a data management method, and a non-transitory recording medium storing a program, which manage data generated plural processing units that perform processing.

BACKGROUND ART

In using a wide variety of vast data group, a large number of data processing programs operate for the purpose of providing a variety of services using the data group. Those data processing programs each access to the data group, process and convert the accessed data, and generate various types of data (post-processing data) with added value in order to provide unique services. The computer system may provide a specific service with the use of all or a part of post-processing data generated from the plural data processing programs.

In this case, there is a need to manage a relevance of the post-processing data generated by the plural data processing programs. More specifically, there is a need to manage a consistency of pre-processing data which is a source of the post-processing data generated by the respective data processing programs. For example, if the pre-processing data has been updated, the respective post-processing data generated from one data processing program that has accessed to the pre-processing data before update and another data processing program that has accessed to the pre-processing data after update are different in processing base. As a result, inconsistency may occur in a specific service provided by the computer system.

PTL 1 discloses a method in which a management server monitors an access to electronic data, and allocates metadata indicative of its usage history or processing contents to the electronic data for management if an access occurs. This method realizes a system that extracts original data based on the metadata consolidated by the management server.

PTL 2 discloses a method in which a history management server holds processing history information such as pre-processing data, post-processing data, processing contents, and processing date for a single piece of image data to enable tracking of the processing history of the image data. This method can track the processing history of plural processing result data to manage a relevance between the pre-processing data and the post-processing data.

CITATION LIST

Patent Literature

PTL 1: JP-A-2009-271919
PTL 2: Japanese Patent No. 4793067

SUMMARY OF INVENTION

Technical Problem

In the technique of Patent Literature 1, because a correspondence between the post-processing data and the pre-processing data is not managed, there arises such a problem that if the post-processing data that has been processed or changed is acquired, the processing history of the post-processing data cannot be known.

In the technique of Patent Literature 2, a load for managing the processing history occurs because processing such as detection of both of the pre-processing data and the post-processing data, generation of processing history data that associates the pre-processing data with the post-processing data, and storage of the processing history data is appropriately executed every time processing.

Because the load for managing those processing histories is attributable to the execution of processing in the data processing programs, the load affects the execution per se of the data processing programs. For example, if processing related to the processing history is added to the data processing program during execution of the data processing program, the execution of the processing program is delayed due to the load for managing the processing history. Also, if the amount of data to be treated, the kinds of processing programs, or the execution frequency increases, the load increases due to an increase in throughput related to the management of the processing histories, and an influence of the increased load on the data processing programs also increases.

Solution to Problem

In order to solve the above problem, for example, configurations defined in the claims are applied. The present invention includes plural solutions to the above problem, and is exemplified as follows.

A computer system, including:
a plurality of processing units that acquires pre-processing data, executes given processing on the pre-processing data, and generates post-processing data as a result of the processing;
a data processing unit that allocates, at an opportunity to acquire the pre-processing data by each of the plurality of processing units, an a process ID indicative of ordering of the acquisition, and not updated before and after the given processing of the plurality of processing units to acquired pre-processing data, and stores the post-processing data generated by the given processing of the processing units in a storage device; and
a data management unit that receives a given data search condition, extracts the post-processing data having a process ID equal to or before the process ID that is latest in the post-processing data for each of the processing units and oldest among the respective processing units from the post-processing data that satisfies the data search condition in extracting the post-processing data stored in the storage device, and outputs the extracted post-processing data to a search request source.

Advantageous Effects of Invention

According to the present invention, there can be provided the data management system that manages a correspondence relationship between a specific data processing event and the post-processing data processed by the data processing event as the processing history. Problems, configurations, and advantages other than those described above will become apparent from a description of the following embodiments.

BRIEF DESCRIPTION OF DRAWINGS

FIG. 1 is a schematic view illustrating an outline of a computer system according to a first embodiment of the present invention.

FIG. 2 illustrates a configuration example of a computer system according to the first embodiment.

FIG. 3 is a schematic view illustrating a process ID management table in the computer system according to the first embodiment.

FIG. 4 is a schematic view illustrating a post-processing data group management table in the computer system according to the first embodiment.

FIG. 5 illustrates one specific allocation example of a process ID in the computer system according to the first embodiment.

FIG. 6 illustrates another specific allocation example of a process ID in the computer system according to the first embodiment.

FIG. 7 is a flowchart illustrating a flow of collection processing of pre-processing data in the computer system according to the first embodiment.

FIG. 8 is a flowchart illustrating a flow of management processing of the pre-processing data in the computer system according to the first embodiment.

FIG. 9 is a schematic view illustrating a processing dependent group management table according to a modification of the first embodiment.

FIG. 10 illustrates a configuration example of a computer system according to a second embodiment.

FIG. 11 is a flowchart illustrating a flow of collection processing of pre-processing data according to the second embodiment.

FIG. 12 illustrates a configuration example of a computer system according to a third embodiment.

FIG. 13 is a schematic view illustrating a generation/storage example of repaired data subjected to multistage processing according to the third embodiment.

FIG. 14 is a schematic view illustrating an example of a process ID management table according to the third embodiment.

FIG. 15A illustrates one specific allocation example of a process ID in the computer system according to the third embodiment.

FIG. 15B illustrates another specific allocation example of a process ID in the computer system according to the third embodiment.

FIG. 16 is a flowchart illustrating a flow of collection processing of the pre-processing data including multistage processing according to the third embodiment.

FIG. 17 is a flowchart illustrating a flow of management processing of the post-processing data according to the third embodiment.

FIG. 18 illustrates a configuration example of a computer system according to a fourth embodiment.

FIG. 19 is a schematic view illustrating conversion rule management table in the computer system according to the fourth embodiment.

FIG. 20 is a flowchart illustrating a flow of collection processing of the pre-processing data in the computer system according to the fourth embodiment.

FIG. 21 illustrates a configuration example of a computer system according to a fifth embodiment.

FIG. 22 is a schematic view illustrating data collection schedule management table in the computer system according to the fifth embodiment.

FIG. 23 is a schematic view illustrating a diagram of pre-processing data extraction processing from an external system in the computer system according to the fifth embodiment.

FIG. 24 is a flowchart illustrating a flow of management processing in a pre-processing data collection schedule in the computer system according to the fifth embodiment.

FIG. 25 illustrates a configuration example of a computer system according to a sixth embodiment.

FIG. 26 is a schematic view illustrating a processing cost management table in the computer system according to the sixth embodiment.

FIG. 27 is a schematic view illustrating a screen example displayed on a search request source by processing of the computer system according to the sixth embodiment.

FIG. 28 is a flowchart illustrating a flow of management processing in a data price in a data management device of the computer system according to the sixth embodiment.

DESCRIPTION OF EMBODIMENTS

First Embodiment

Let us consider a case in which plural processing programs that access to the same data source are present, and the respective processing programs issue data processing events, independently. Since the respective processing programs are independent from each other, the events occur at random.

In this case, when it is assumed that the data source is updated, it is unclear whether the events occur for the same data source, or not, depending on timing when the respective events occur.

For example, it is assumed that two given processing programs using both data of an image A and a keyword B stored in the data source are present, and those programs operate, independently. Whether the respective processing programs have generated the events (for example, data acquisition event/data crawl) for the same data source before update, or not, can be discriminated by managing whether the processing per se of both those programs have been completed, or not. If only the processing of one processing program is completed, whether the other processing program generates the event for the same data source is unknown in authenticity (the image A and the keyword B are not included in the same data source).

Conversely, if the processing of both the processing programs is completed, it can be determined that the image A and the keyword B are included in the same data source. That is, in order to ensure that collection results crawled from the data source by the respective processing programs match each other, there is a need to manage data after event processing to be acquired in the respective programs. In order to realize this management, there is a need to manage the post-processing data processed by the event, and the processing history of data processing events of the respective processing programs in association with each other.

However, to add processing for managing the processing history during execution of the processing program is high load, and causes a processing delay. Further, there is a need to subject the respective processing programs to modification for managing the processing history, and a problem of flexibility also remains.

In a first embodiment, a description will be given of a method in which if a data processing event (for example, data acquisition/data crawl) for the data source is generated, a process ID that can uniquely identify the data processing event, and is not changed before and after the processing of the processing program is generated, the process ID is allocated to the data to be processed before being used for the event, and the processed data is managed by the process ID to manage whether the data acquired from the data source is consistent between the processing programs, or not.

[Outline]

FIG. 1 illustrates an outline configuration of a computer system according to the first embodiment of the present invention.

A data processing unit 10 has programs A 12a to C 12c that executes plural independent processing. The respective programs issue events to a data source 4 at arbitrary timing. In the description, it is assumed that the issued events are data acquisition (data crawling). In the data source 4, a pre-processing data region 30 which is data (hereinafter called "pre-processing data") before being acquired by the program A 12a is ensured, and a post-processing data storage region 40 which is acquired data (hereinafter called "post-processing data") after being acquired by the data acquisition event of the respective programs is ensured. First, the program A 12a requires the data source 4 to acquire data, and acquires pre-processing data X 31a. The data processing unit 10 generates a process ID 45a ("1" in the figure), and simultaneously manages the process ID 45a, and "program A" which is an event request source in association with each other in a process ID management table 17. The pre-processing data X 31a is transmitted to the program A 12a in a state where the process ID 45a is added to the pre-processing data X 31a, and used in given processing of the program A 12a.

The program A 12a that has received the pre-processing data X 31a added with the process ID 45a generates a post-processing data X 41a after given processing has been executed. In this situation, the process ID 45a is continuously added to the post-processing data X 41a as a normal ID without being affected by the given processing. Thereafter, the post-processing data X 41a is stored in the post-processing data storage region 40.

Then, the program B 12b requires the data source 4 to acquire data. The data processing unit 10 generates unique process ID 45b ("2" in the figure) different from the event of the above program A 12a, and manages the process ID 45b in association with "program B" which is an event issuance source in the process ID management table 17. The process ID 45 is newly generated by incrementing the latest (maximum value) process ID by one in the process ID management table 17.

A post-processing data Y 41b used in the given processing of the program B 12b is stored in the post-processing data storage region 40 in a state where the post-processing data Y 41b holds the process ID 45b.

The data processing unit 10 repeats the same processing every time data is acquired by the respective programs A 12a to C 12c.

Meanwhile, upon receiving a search request including a given search condition from the search request source, a data management unit 20 searches a post-processing data 41 group added with the process ID 45, and extracts post-processing data 41 satisfying the search condition.

In this situation, the data management unit 20 extracts the process ID 45 added to the extracted post-processing data 41, and executes processing grouped for each of program types. This result is a post-processing data group management table 25.

In the post-processing data group management table 25, the process ID is grouped for each of the programs A 12a to C 12c. For that reason, data used for the processing of the respective programs can be discriminated from the process ID. For example, it is found that data used by the event of the program A 12a is data when the process ID is "1" and "5".

Since the process ID 45a to 45c are allocated and managed by the data processing unit 10 in issuance order of the events, the data management unit 20 extracts the respective latest (maximum value) process ID 45 from the process ID 45 of the respective groups, and obtains the process ID (hereinafter called "all-processing completion ID 55") which is oldest (minimum value) among the groups in the extracted latest process ID ("5" in the figure). Then, the data management unit 20 obtains the process ID 45 group except for the process ID 45 newer (larger in value) than the all-processing completion ID 55.

It is found that in the post-processing data 41 corresponding to the post-processing ID 45 group obtained as described above, the pre-processing data whose consistency is ensured is processed in the data acquisition events issued by the processing programs A 12a to C 12c. The data management unit 10 provides (transmits) only the post-processing data 41 generated from the consistent pre-processing data to the search request source.

Also, a list of the all-processing completion ID 55 or ID after removal of an intermediate state can be output according to a request from the search request source or a system manager (not shown).

In the computer system 1 according to the first embodiment, the universal process ID 45 that is allocated immediately before the data acquisition event is generated for the pre-processing data 31a, and not affected by the subsequent processing of the program A 12a is carried out to the post-processing data, thereby being capable of managing the consistency of the pre-processing data which is a source of the post-processing data 41 without managing the processing per se of all the programs A 12a to C 12c.

Further, because the data processing unit 10 executes processing related to generation and allocation of the process ID 45, there is advantageous in that a load is applied to the given processing such as the program A 12a. Further, such an advantage to reduce the development effort of the processing programs can be expected with no need to sequentially describe codes for executing the generation and addition of the process ID such as the program A 12a.

The outline is described above.

FIG. 2 illustrates the more detailed configuration of the computer system 1 according to the first embodiment.

The computer system 1 is a server device including a CPU 2, a memory 3 as a main storage, a storage device 4 as an auxiliary storage, an input/output device 5 that conducts various types of input/output such as a keyboard, a pointing device, a display monitor, or a printer, and an I/F 6 that communicates with an external device through an LAN or the Internet in a wired or wireless manner. The input/output device 5 may be installed outside of the computer system 1, and be operable from a mobile terminal through the I/F 6.

The memory 3 includes, for example, the data processing unit 10 that is a function unit realized in cooperation with the CPU 2 and a program, and the data management unit 20.

The data processing unit 10 includes a processing program execution unit 12 in which the various independent programs A 12a to C 12c operate, a pre-processing data collection unit 15 that acquires data from the storage device 4 according to a request from those programs, a process ID allocation unit 14 that generates the unique process ID 45 for the collected data, a process ID holding unit 13 that holds the process ID management table 17 for managing the process ID in association with the program A 12a which is a data collection request source, and a post-processing data storage unit 16 that stores the post-processing data 41 which is data that has been used for the given processing such as the program A 12*a* into the storage device 4 in a state where the process ID 45 is allocated to the post-processing data 41.

The programs A 12*a* to C 12*c* are function units that conduct the processing independent from each other. The respective programs acquire various pieces of necessary data for the respective processing (for example, various pieces of real data or metadata in various fields are conceivable such as data necessary for electronic medical records such as attributes, a medical history, a CT, or an X-ray image of a patient in a medical field, various pieces of sensor data in factories and plant management, messages or moving image data in an SNS (social network system) field, customer data or a transaction history in a financial field, and customer attributes and a purchase history in a distribution field) from the storage unit 4, and conduct the respective processing.

FIG. 3 schematically illustrates the process ID management table 17. The process ID management table 17 is information that includes a process ID item 18 and a request source item 19, associates the unique process ID 45 generated by the process ID allocation unit 14 for the pre-processing data acquired by a data acquisition request of each program with the data acquisition request source, and manages the process ID 45 and data acquisition request source in ascending order. This embodiment describes an example using the table. However, the present invention is not limited to this example, but may hold a list structure. Also, even if the process ID 45 is not managed in the ascending order, various systems can be applied if the ordering can be determined.

Also, the process ID 45 may use a time at which the data acquisition event is generated. Further, except that the process ID is newly generated by the process ID allocation unit 14, an existing identifier provided in a pre-processing data 31 may be used. In this case, the process ID allocation unit 14 and the process ID holding unit 13 can extract the above identifier from the pre-processing data 31, and manage the ordering. Specifically, an access time or an update time included as the metadata of the data may be used as the process ID, or path information indicative a storage place of the data may be used as the process ID, and the path information may be managed in order of being a processing target of the data acquisition events.

The data management unit 20 includes the CPU 2, a search condition reception unit 21 that is a function unit realized in cooperation with the program, a post-processing data collection unit 22, a processing history management unit 23, a post-processing data group management table 24, and a search result transmission unit 25. Various types of search results are calculated with the use of the process ID management table 17 managed by the data processing unit 10.

The search condition reception unit 21 receives the search request input through the input/output device 5. A given search condition is included in the search request, such as a request for extracting the post-processing data acquired by the data acquisition event of the processing programs A 12*a* to C 12*c* for each program, and a search request for the post-processing data 41 acquired in the data acquisition event of all the processing programs A 12*a* to C 12*c*.

The post-processing data collection unit 22 collects the post-processing data 41 satisfying the search condition together with the process ID 45 added thereto according to the reception of the search request by the search condition reception unit 21.

The processing history management unit 23 groups the post-processing ID 45 acquired by the post-processing data collection unit 22 for each of the programs A 12*a* to C 12*c* with reference to the process ID management table 17, and creates the post-processing data group management table 24.

FIG. 4 schematically illustrates the post-processing data group management table 24. The post-processing data group management table 24 includes group items 26 to 28 of the respective programs A 12*a* to C 12*c*, a latest process ID item 50, a process ID list item 51, and an ID list item after removal of an intermediate state 52. In the process ID list item 51, the process ID 45 of the post-processing data 41 searched by the post-processing data collection unit 22 on the basis of the search condition is stored. In the latest process ID item 50, the latest (maximum value) process ID 45 is stored on a group basis of the process ID list item 51.

In the ID list item after removal of the intermediate state 52, the process ID registered in the process ID list item 51 is stored except for the process ID newer (larger in value) than the all-processing completion ID 55 which is the oldest (minimum value) latest process ID among the latest process ID 50 of all the groups. For example, when the all-processing completion ID 55 is "5" in the process ID of the latest process ID list 50, the process ID 45 ("1", "2", "3", "4", "5") of 5 or lower are stored.

The search result transmission unit 25 outputs the post-processing data corresponding to the process ID 45 stored in the ID list item after removal of an intermediate state 52 as the search results.

The storage device 4 is formed of, for example, an HDD or an SSD, and holds various pieces of data used in the programs A 12*a* to C 12*c*. The storage device 4 includes two storage regions of the pre-processing data storage region 30 that holds pre-processing data X31*a*, Y31*b* . . . , and the post-processing data storage region 40 that stores post-processing data X41*a*, Y41*b* . . . . The pre-processing data 31 in the pre-processing data storage region 30 is appropriately updated (added, deleted, and overwritten).

The above-mentioned process ID 45*a* to 45*c* are not allocated to the pre-processing data X 31*a*, 31*b* . . . . The post-processing data 41*a* to 41*c* are hold in state where the process ID 45*a* to 45*c* are allocated to the post-processing data 41*a* to 41*c*. The process ID 45*a* to 45*c* allocated once are continuously held without being deleted in the subsequent processing of the programs A 12*a* to C 12*c*.

FIGS. 5 and 6 schematically illustrate an example of the post-processing data 41 added with the process ID 45.

As illustrated in FIG. 5, when a data structure includes a header part that stores control information therein, and a body part that stores real data therein, "process ID=1" may be written into the header part as the process ID 45 (numerical values are appropriately changed according to a processing order).

Also, as illustrated in FIG. 6, subsequent to a description of <Source>~</Source> indicative of the location of data, "<ProcessID>1</ProcessID>" is described between <Metadata> and </Metadata> as the metadata, and the process ID 45 may be allocated thereto (numerical values are appropriately changed according to a processing order).

As described above, the time at which the pre-processing data is acquired may be used as the process ID.

A description will be given of a flow of processing in the computer system 1 with the above configuration in detail.

FIG. 7 illustrates a processing flow of the data processing unit 10.

In S101, the pre-processing data collection unit 15 receives a pre-processing data acquisition request issued from any one of the programs A 12*a* to C 12*c* (received from an acquisition request from the program A 12*a*).

In S103, the process ID allocation unit 14 acquires the latest (maximum value) process ID 45 with reference to the process ID management table 17 of the process ID holding unit 13, and generates the new process ID 45*a* incremented by one (if there is no latest process ID in the process ID management table 17, "1" is generated. In this example, "1" is applied.).

In S105, the process ID holding unit 13 associates the new process ID with identification information (program name) of the program A 12*a* which is a data acquisition request source, and additionally registers the associated information to an end of the process ID management table 17.

In S107, the pre-processing data collection unit 15 collects the required pre-processing data X 31*a*, adds the new process ID 45*a*, and transmits the pre-processing data X 31*a* to a processing program execution unit 11. The program A 12*a* executes given processing on the acquired pre-processing data X 31*a*.

In S109, the post-processing data storage unit 16 stores the post-processing data X 41*a* generated as a result of the given processing in the post-processing data storage region of the storage device 4. In this situation, the post-processing data X 41*a* is stored in a state where the program that has executed the processing can be identified. Specifically, the post-processing data storage region 40 may be ensured for each processing program, or information on the program A 12*a* may be allocated as the metadata of the post-processing data X 41*a*.

The flow of processing in the data processing unit 10 is described above.

FIG. 8 illustrates a flow of processing in the data management unit 20.

First, in S151, the post-processing data collection unit 22 collects the post-processing data 41 that matches the condition together with the attendant process ID from the post-processing data storage region 40 in response to the search request input to the search condition reception unit 21 through the input/output device 5.

In S153, the processing history management unit 23 groups and manages the post-processing data 41 for each of the programs A 12*a* to C 12*c* that have executed the processing with reference to the process ID management table 17, and extracts the latest (maximum) process ID 45 for each of the groups. For example, as shown in the post-processing data group management table 25 of FIG. 4, the post-processing data 41*a* implemented by the program A belongs to the program A group 26, and the latest process ID is "5", and the process ID 45 associated with the respective post-processing data 41 belonging to the program A group 26 is recorded as "1" and "5" in the process ID list item 51. The same processing is also conducted on the other groups.

In S155, the processing history management unit 23 acquires the oldest (minimum value) process ID in the respective groups as the all-processing completion ID 55 in the latest process ID 45 extracted in the respective groups. For example, in the post-processing data group management table 25, the all-processing completion ID 55 becomes "5" smallest in the value in the latest process ID.

In S157, the processing history management unit 23 removes the process ID 45 newer (larger) than the all-processing completion ID 55 from the collection data, records the result in the ID list item after removal of an intermediate state 52, and transmits the result to the search result transmission unit 22. For example, in the post-processing data group management table 25, it can be determined that the pre-processing data 31 before the post-processing data 41 having the process ID 45 of "5" or lower which is the all-processing completion ID 55 is processed is also to be subjected to all other processing. On the other hand, the pre-processing data 31 before the post-processing data 41 that holds the process ID 45 larger than "5" in the process ID 45 is processed may not be to be subjected to the processing by the program A 12*a*. The post-processing data 41 in this state is removed.

In S159, the search result transmission unit 25 transmits, to the search request source, the post-processing data 41 corresponding to the process ID 45 stored in the ID list item after removal of an intermediate state 52 among the post-processing data 41 searched by the post-processing data collection unit 22 in S151. For example, the search result sent onto the screen is displayed on the search request source.

A flow of processing in the data management unit 20 is described above.

In this way, in the computer system 1 according to the first embodiment, at the time of acquiring data of the programs A 12*a* to C 12*c*, the unique and universal process ID 45 which is not modified in the processing of those programs is generated and allocated, and it can be managed whether the pre-processing data acquired in the respective programs A 12*a* to C 12*c* is consistent, or not, on the basis of the all-processing completion ID 55. This means that only the post-processing data 41 that can be obtained as a result of executing the data acquisition by all the programs A 12*a* to C 12*c* on the pre-processing data can be extracted and managed.

Also, in the computer system 1, because not the program A 12*a*, but the process ID allocation unit 14 generates the process ID 45, and allocates the process ID 45 to the pre-processing data 31, and the process ID 45 of the post-processing data 41 is used by the processing history management unit 23, the influence of the program A 12*a* per se is not affected. At the same time, there is no need to add a function (description of the program) of managing the process ID 45 to the programs A 12*a* to C 12*c* per se, resulting in such an advantage to reduce the development effort of the programs.

Also, in the computer system 1, because the process ID 45 is held in the post-processing data 41 without being modified due to the various processing in the processing program execution unit 11, the process ID 45 can be used as the identification information unified within the computer system 1.

(Modification of First Embodiment)

The present invention is not limited to the first embodiment, but can be applied with various configuration without departing from the spirit of the present invention. For example, in the computer system 1, the processing history of the post-processing data 41 and the data acquisition event are managed in all of the programs A 12*a* to C 12*c*. The processing history can be managed between only the respective specific programs.

FIG. 9 schematically illustrates a dependent group management table 56 that defines a dependency between the specific programs. In this table, the respective programs having a dependency on each other are grouped, and a correspondence between a dependent group ID and identification information (program name in this example) on a processing program having a dependency is defined for the groups.

The dependent group management table 56 is provided in the data management unit 20. In the search process of the post-processing data illustrated in FIG. 8, a value of the dependent group ID item 57 is allocated to the respective processing programs having the dependency in the dependent group management table 56, and the processing programs having the same dependent group ID may execute the processing from S153 (FIG. 8).

As a result, the search result that ensures the consistency of the pre-processing data between the specific programs can be provided.

Second Embodiment

A computer system 60 according to a second embodiment will be described. The computer system 1 according to the first embodiment is described with the single physical computer as an example. In this example, the programs A 12a to C 12c in the computer system 1 may be provided as another computer resource. For example, some processing executed by a business program (including applications and middleware which is a base of those applications) may frequently have functions such as search. The server computer can be frequently arbitrarily added or deleted on the business program basis with a shared data source. In the single physical computer according to the first embodiment, the addition or deletion of the program may be associated with execution stop of other programs, or restart of the computer for the purpose of expanding memory resources or CPU resources, thereby causing a negative effect of processing as an overall computer system.

In a second embodiment, a description will be given of an example in which the present invention is applied to a computer system having a configuration in which the respective programs are provided by computers physically independent from each other, and those programs issue the data acquisition events to the identical data source.

Also, in the computer system according to the second embodiment, the data acquisition requests from the programs A 12a to C 12c can be applied to not only the pre-processing data 31 but also the post-processing data 41. Any data to be acquired can be arbitrarily set by the programs A 12a to C 12c.

In the following description, the equivalent elements to those described in the first embodiment are denoted by identical symbols, and a detailed description thereof will be omitted.

FIG. 10 illustrates a configuration of the computer system 60 according to the second embodiment. One of the features of the computer system 60 resides in that the programs A 12a to C 12c are executed by execution computers 70a to 70c physically independent from each other. Another feature of the computer system 60 resides in that the function unit of the data processing unit 10 according to the first embodiment is provided in a data storage device 90, and the respective function units of the data management unit 20 are provided in a data management device 80. Because the respective execution computers 70a to 70c ensure computer resources for running their own programs, there is advantages in that the respective execution computers 70a to 70c do not affect the system (temporal) stop of the overall system associated with the addition/deletion to the computer system 60.

The data management device 80 is a computer device including a CPU 81, a memory 22, a storage device 83, and an I/F 84 for external communication. The memory 22 includes the search condition reception unit 21, the post-processing data collection unit 22, the post-processing data group management table 24, and the search result transmission unit 25.

The execution computers 70a to 70c are computer devices each including a CPU 71, a memory 72, a storage device 73, and an I/F 74 that communicates with the external. This example uses a configuration having three execution computers, but the number of execution computers can appropriately increase or decrease according to a system requirement of the computer system 60. The programs A 12a to C 12c can operate in the memory 72. The execution computers 70a to 70c has data stored in a storage unit 93 of the data storage device 90 as a shared data source. The execution computers 70a to 70c acquire (crawl) the pre-processing data 31 or the post-processing data 41 in the storage unit 93 at arbitrary timing, and use the acquired data in the respective programs A 12a to C 12c.

The data storage device 90 is a computer device including a CPU 91, a memory 92, the storage unit 93, and an I/F 94 that communicates with the external, and can employ, for example, a server device or a storage device. The memory 92 includes the pre-processing data collection unit 15, the process ID allocation unit 14, the post-processing data storage unit 16, the process ID holding unit 13, and the process ID management table 17, but is different from the first embodiment in that a processing data control unit 95 is newly provided.

Upon receiving a data acquisition request from the execution computers 70a to 70c, the processing data control unit 95 searches data responsive to the request from the data group stored in the pre-processing data storage region 30 or the post-processing data storage region 40, or both of these region, and transmits the searched data to the execution computer A 12a. In more detail, if the request from the execution computers 70 or the like is pre-processing data (data that has not yet been acquired) stored in the pre-processing data storage region 30, the processing data control unit 95 delivers the processing to the pre-processing data collection unit 15. If the request is data (data that has been acquired) stored in the post-processing data region 40, the processing data control unit 95 acquires the required post-processing data from the post-processing data storage region 40, and outputs the post-processing data to the execution computer which is a request source.

The computer system 60 is configured as described above.

In the second embodiment, a description will be given of an example in which the data management device 80 and the data storage device 90 are configured by different computer devices. However, the present invention is not limited to this configuration, but both of those devices can be configured within the same computer.

Further, in addition to a configuration in which one computer device is provided for one program, the execution computer 70 can be configured so that plural virtual computers are provided for a single physical computer as a virtual computer. In this case, the physical computer may be preferably provided with a function of allowing the computer resources such as a CPU or a memory to be autonomously controllable in increasing or decreasing the virtual computers.

FIG. 11 illustrates a processing flow of the data storage device 90 in the computer system 60.

In S201, upon receiving the data acquisition request from any one of the programs A 12a to C 12c in the execution computers 70a to 70c (data acquisition request from the program A 12a), the data control unit 95 determines whether the request is an acquisition request for the pre-processing data 31, or an a acquisition request for the post-processing data 41. If the request is the acquisition request for the pre-processing data 31 (yes in S201), the flow proceeds to S203, and if the request is the acquisition request for the post-processing data 41 (no in S201), the flow proceeds to S213.

In S203, the pre-processing data collection unit 15 receives an instruction for collecting the pre-processing data 31 from the data control unit 95.

In S205, the process ID allocation unit 14 acquires the latest (maximum value) process ID with reference to the process ID management table 17 of the process ID holding unit 13, and generates the new process ID 45a incremented by one (if there is no latest process ID in the process ID management table 17, "1" is generated. In this example, "1" is applied.). The process ID allocation unit 14 associates the acquired process ID with identification information (program name) of the program A 12a which is a data acquisition request source, and additionally registers the associated information to an end of the process ID management table 17.

In S207, the pre-processing data collection unit 15 collects the required pre-processing data X 31a, adds the new process ID 45a, and transmits the pre-processing data X 31a to the execution computer A 12a of a request source. The program A 12a executes given processing on the acquired pre-processing data X 31a.

In S209, the post-processing data storage unit 16 receives the post-processing data X 41a generated by given processing from the execution computer 70a, and stores the post-processing data X 41a in the post-processing data storage region 40 in a state where the new process ID 45a is added to the post-processing data X 41a. In this situation, the storage unit 93 stores the post-processing data X 41a in a state where the program that has processed the post-processing data X 41a can be identified.

On the other hand, in the determination of S201, if it is determined that the data collection request target is not the pre-processing data, the processing data control unit 95 accesses to the post-processing data storage region 40, collects the post-processing data matching the search condition of the request, and transmits the collected post-processing data to the execution computer 70a which is the request source in S213. A flow of processing in the data storage device 90 is described above.

The process ID management table 17 managed as described above conducts the processing history management that can confirm the conformity of data used in the respective execution computers 70a to 70c in the data management device 80 as in the first embodiment.

As described above, according to the computer system 60 of the second embodiment, because the execution computer 70 and the storage of data before and after the processing can be realized by the computers different from each other, the computer that realizes the execution of the processing can be added to the system without stopping the device that realizes the storage of the data before and after processing.

Also, because data retention and the management of the process ID 45 in the plural execution computers 70 are consolidated by the data storage device 90, even if the configuration of the execution computer 70 is more complicated, the data retention and the process ID 45 can be managed by using the process ID unified in the computer system 60.

Further, even in the computer system 60, the consistency of the pre-processing data among the programs A 12a to C 12c can be managed with the use of the process ID 45 as in the first embodiment.

Third Embodiment

In the first and second embodiments, there is conceivable a case in which the post-processing data 41 generated by given processing of the programs A 12a to C 12c is subjected to the data acquisition request for the subject or another program. Hereinafter, a process in which the post-processing data acquired as the processing target once, and generated by data processing (including machining) caused by the program of one acquisition source is again acquired to generate the post-processing data generated by the data processing (including machining) caused by the program of another acquisition source is called "multistage process". In the multistage process, the post-processing data acquired and generated previously, and the post-processing data acquired and generated currently are different in a data group to be acquired from each other.

In a third embodiment, a description will be given of a computer system 100 that manages the consistency of the post-processing data 41 up to the previous time and until this time when the multistage process occurs.

The computer system 100 is based on the configuration of the computer system 60 of the second embodiment, but the management of the processing history in the multistage process is also applicable to the computer system 1 of the first embodiment. Hereinafter, particularly, portions different in the configuration will be described, and portions common in function and element are denoted by the same symbols, and a detailed description thereof will be omitted.

FIG. 12 illustrates a configuration of the computer system 100. In the computer system 100, the data management device 80 receives a search request including a search key and a search condition from a search request source. In the data management device 80, a post-processing data 41 group corresponding to the search key is extracted, and in the post-processing data satisfying the search condition in the extracted post-processing data 41 group, the post-processing data taking the consistency of data by the multistage process into account is obtained as the search result. This process is different from the other embodiments.

Further, the computer system 100 can process the data acquisition request to the post-processing data from the programs A 12a to C 12c in the data storage device 90, and if the data acquisition request to the post-processing data is conducted, the new process ID 45 is generated and allocated to the post-processing data. This is different from the other embodiments.

First, differences in the data storage device 90 will be described in detail.

In a processing data control unit 120, it is determined whether data to the data acquisition request issued from any one of the execution computers 70a to 70c is the pre-processing data or the post-processing data. This determination is made according to whether a storage destination of data in the data storage device 90 is the pre-processing data storage region or the post-processing data storage region 40. The determination may be conducted according to whether the process ID 45 allocated to the post-processing data 41 is present, or not.

If it is determined according to the processing data control unit 120 that the target of the acquisition request is the pre-processing data 31, as in the other embodiments, the given pre-processing data 31 is acquired by the pre-processing data collection unit 15, the process ID 45 obtained by incrementing the latest process ID of the process ID management table 17 by 1 is generated, and the process ID 45 is transmitted to the execution computer 70 of the data acquisition request source in a state where the process ID 45 is allocated to the pre-processing data. At the same time, the process ID and the acquisition request source is recorded in the process ID management table 17.

The data transmitted to the execution computer is subjected to given processing (machining) by the program A 12a to generate the post-processing data 45 in the state where the process ID 45 is allocated to the data. Thereafter, the post-processing data is stored in the post-processing data storage region by the post-processing data storage unit 16.

On the other hand, if it is determined that the data acquisition target from the execution computer 70 is the post-processing data, the process ID 45 obtained by incrementing the latest process ID 45 in the process ID management table 17 by one is generated by the processing data control unit 120, and the post-processing data 41 is transmitted to the execution computer 70 of the acquisition request target in a state where the process ID 45 is allocated to the post-processing data 41. At the same time, the generated process ID and the acquisition request source are recorded to an end of the process ID management table 17.

FIG. 13 schematically illustrates a generation/storage example of the post-processing data in which the post-processing data is again acquired, and the multistage process is conducted.

First, upon receiving the acquisition request for the pre-processing data from the program A 12a of the execution computer 70a, the pre-processing data X 31a is acquired from the pre-processing data storage region 30, and the process ID 45a is allocated to the pre-processing data X 31a. Thereafter, a post-processing data X 40a is generated by the processing of the program A 12a, and the post-processing data X 41a is stored in the post-processing data storage region 40. Subsequently, similarly, the pre-processing data Y 31b and the pre-processing data Z 31c are stored in the post-processing data storage region 40 as the post-processing data Y 41b and the post-processing data Z 41c.

Subsequently, it is assumed that the pre-processing data control unit 120 receives the acquisition request for the post-processing data X 41a from the program B 12b. The processing data control unit 120 acquires a process ID 45c ("3") which is the latest process ID at that time in the process ID management table 17 to generate a process ID 45d of "4" obtained by incrementing the process ID 45c by 1. The generated process ID 45d ("4") is added and allocated to the post-processing data X 40a, and transmitted to the program B 12b. A post-processing data XX 41d processed by the program B 12b is stored in the post-processing data storage region 40. Subsequently, similarly, the post-processing data Y 41b and the post-processing data Z 41c are also stored in the post-processing data storage region 40 as a post-processing data YY 41e and a post-processing data ZZ 41f. FIG. 14 illustrates an example of the process ID management table 17 in the example of FIG. 13.

FIGS. 15A and 15B illustrate an implementation example in which the process ID 45 is added to the post-processing data 41. FIG. 15A illustrates an example in which the process ID is added to the header part in ascending order. "ProcessID=3" is a process ID added and allocated. FIG. 15B illustrates an example in which the process ID is added as metadata. "3" in a region surrounded by "<IDList>"~"</IDList>" is a process ID added and allocated.

Changes of the data management device 80 will be described in detail.

In the data management device 80, the processing contents of the post-processing data collection unit 22 and the processing history management unit 23 are particularly different from the other embodiments.

In the post-processing data collection unit 22, the search process to the search request including a given search key from the search request source is conducted on the overall post-processing data 41 stored in the post-processing data storage region 40.

In the processing history management unit 23, in the post-processing data 41 group extracted as the search result by the post-processing data collection unit 40, only the post-processing data that is the data acquisition request target from the execution computers 70a to 70c is transmitted to the search request source as the search result. That is, only the post-processing data 41 generated by the multistage process is returned as the result of the search request.

In the processing history management unit 23, the post-processing data satisfying the search contents is acquired together with the process ID 45 allocated, respectively, from the post-processing data storage region 40 according to the search request. Thereafter, the latest process ID is extracted from the acquired post-processing data 41 group. In the processing history management unit 23, request source (program name) of the extracted latest process ID 45 is extracted on the basis of the process ID management table 17. The post-processing data 41 having the same request source name as the request source (program name) and having the process ID 45 issued to the latest post-processing data 41 shift in the process ID management table 17 is transmitted to the search request source as the search result.

For example, in an example of FIG. 13, it is assumed that the post-processing data 41 corresponding to the search key includes the post-processing data X 41a and the post-processing data XX 41d (process ID is "1" and "4"). Since the latest process ID is "4", the acquisition request source name of the process ID "4" is acquired with reference to the process ID management table 17. In this example, the acquisition request source name is "program B". The post-processing data 41 in which the acquisition request source is the program B similarly in the process ID management table 17 is the post-processing data YY 41e and the post-processing data ZZ 41f. Those data has the same problem B which is the acquisition request source, and has the process ID "5" and "6" after "4" which is the latest process ID. In the processing history management unit 23, the post-processing data 41 having the process ID 45 of "4", "5", and "6" is transmitted to the search request source by the search result transmission unit 25.

The post-processing data XX 41d is data subjected to the multistage process on the basis of the post-processing data X 41a. For that reason, data corresponding to the search key included in the search request is included in the post-processing data X 41a and the post-processing data XX 41d. Hence, the post-processing data having the latest process ID 45 in the post-processing data group including the data corresponding to the search key becomes the post-processing data generated by the multistage process.

In the above configuration, a flow of processing in the computer system 100 will be described with reference to flowcharts of FIGS. 16 and 17.

FIG. 16 illustrates a processing flow of the data storage device 90.

In S301, the processing data control unit 120 receives issuance of a data acquisition event from any one of the execution computers 70a to 70c.

In S303, the processing data control unit 120 allows the process ID allocation unit 14 to refer to the process ID management table 17, and generates a new process ID obtained by incrementing the latest (maximum value) process ID by 1. Then, the processing data control unit 120 adds the new entry to the process ID management table 17, and records the new process ID and the request source program name in association with each other.

In S305, the processing data control unit 120 determines whether the acquisition destination is the pre-processing data storage region 30, or the post-processing data recording region 40, on the basis of the recording area of the data acquisition destination. If the acquisition destination is the post-processing data storage region 40, the flow proceeds to S307, and if the acquisition destination is the pre-processing data storage region 30, the flow proceeds to S313.

In S307, the processing data control unit 120 acquires the given post-processing data 41 from the post-processing data storage region 40.

In S309, the process ID allocation unit 14 additionally allocates the new process ID generated in S303 to the acquired post-processing data 41, and transmits the post-processing data 41 to the execution computer 70 of the request source.

In S311, the post-processing data storage unit 16 receives the post-processing data 41 generated by given processing of the program A 12a such as the execution computer 70a, and stores the post-processing data 41 in the post-processing data recording region 40 together with the allocated or additionally allocated process ID 45.

On the other hand, when the flow proceeds to S313, the pre-processing data collection unit 15 collects the pre-processing data from the pre-processing data recording region 30, and proceeds to the processing of S309.

A flow of the operation of the data storage device 90 is described above.

FIG. 17 illustrates a processing flow of the data management device 80.

In S351, the search condition reception unit 21 receives the search request including the given search key from the search request source.

In S353, the post-processing data collection unit 22 searches the post-processing data 41 group of the post-processing data storage region 40 on the basis of the search key, and extracts the post-processing data corresponding to the search key together with the attendant process ID 45.

In S355, the processing history management unit 23 extracts the latest process ID 45 from the process ID 45 of extracted post-processing data 41 group.

In S357, the processing history management unit 23 acquires the process ID management table 17, and extracts the acquisition request source (program name) corresponding to the latest process ID extracted in S355.

In S359, the processing history management unit 23 extracts the process ID having the same acquisition request source (program name), and larger in value than the latest process ID extracted in S355 in the process ID management table 17.

In S361, the processing history management unit 23 extracts the post-processing data 45 having the process ID larger in value than the latest process ID, which is extracted in S359, from the post-processing data storage region 40.

In S363, the processing history management unit 23 returns the post-processing data 45 having the latest process ID, and the post-processing data 45 having the process ID larger in value than the latest process ID to the search request source through the search result transmission unit 25.

A flow of the operation in the data management device 80 is described above.

As described above, according to the computer system 100 of the third embodiment, in the post-processing data 41 which is subjected to the multistage process, the post-processing data that is subjected to the multistage process and the subsequent post-processing data that is subjected to the multistage process in the post-processing data corresponding to the given search key can be managed.

Fourth Embodiment

In a fourth embodiment, a description will be given of a computer system 150 having a configuration that can use plural data sources storing data different in data format. In the computer system, in order to increase the types or amount of data, it may be preferable that data managed by the external computer system can be used by a subject computer system.

However, if the format of data managed by the external system is different from the data format of the subject computer system, data may not be processed by the same processing program.

Further, the use of data managed by the external system becomes enormous in the amount of data, and a load for managing the processing history such as the data acquisition event to the data also increases.

Under the circumstance, the computer system 150 according to the fourth embodiment has a conversion function of converting the data format into a data format that can be used by the respective processing programs in the data storage device 90 even in the different data format as one of the features. The conversion function has a function unit (external system data collection unit 151, data conversion unit 152, conversion rule holding unit 153, and conversion program group 155) that realizes ETL (Extruct/Transform/Load) in cooperation with software and a CPU.

FIG. 18 illustrates a configuration of the computer system 150. The data management device 80 and the execution computers 70a to 70c in the computer system 150 have the same function configuration as that of the computer system in the first to third embodiments. The data recording device 90 has a data conversion function for enabling data of external systems 170a and 170b to be used in the computer system 150, and a function of managing the process ID of data including the data of the external systems, which is particularly different from the other embodiments.

The external systems 170a and 170b are computer systems each having a storage device that stores data therein, and can communicate with the data storage device 90 through a communication line. Data (character string data, image data, etc.) different in data format is stored in the external systems 170a and 170b. Also, the data stored in the external systems 170a and 170b is pre-processing data that is not subjected to the data acquisition request from the programs A 12a to C 12c as with the pre-processing data 31a to 31c of the pre-processing data storage region 30. The external systems 170a and 170b transmits appropriate pre-processing data L 33a to R 35b to the data storage device 90 in response to a request from the data transmission/reception unit 151 in the data storage device 90, which will be described later.

Also, in the external systems 170a and 170c, data held within the external systems is appropriately updated from an access point (not shown) on the external system basis.

In this example, two external systems are provided, but the number of external systems is arbitrary according to the specification of the system.

The data storage device 90 newly includes the external data collection unit 151, the data conversion unit 152, the conversion rule holding unit 153, a conversion rule table 154, and the conversion program group 155.

The external data collection unit 151 acquires data corresponding to a request from the external systems 170a and 170b in response to the data acquisition request received from the program A 12a through a processing data control unit 121. The external systems 170a and 170b search the storage regions of the subject device according to the request from the external data collection unit 151, and returns the search results to the external data collection unit 151.

The data conversion unit 152 converts the data format of the pre-processing data L 33a acquired from the external systems 170a and 170b with a conversion program corresponding to the respective data formats. In more detail, the conversion rule holding unit 153 has the conversion rule table 154 representing a correspondence relationship between the data formats and the conversion programs thereof in advance, and calls an appropriate conversion program from the conversion program group 155 corresponding to the data format of a model according to the conversion rule table 154, and generates the pre-processing data converted into a given data format. The pre-processing data L 33a converted in the data format is thereafter held in the process ID allocation unit 16.

FIG. 19 schematically illustrates the conversion rule management table 154. The conversion rule management table 154 has a data format item 160 and a conversion program item 161. For example, if the data format is "character string", the conversion program corresponds to "A conversion program".

Returning to FIG. 18, also in the computer system 150, the pre-processing data X 31a acquired from the pre-processing data storage region 30, and the pre-processing data L 33a acquired from the external systems 170a and 170b, and converted in the data format are allocated with the process ID 45 by the process ID allocation unit 14, and transmitted to the program A 12a of the request source through the processing data control unit 121.

Likewise, the post-processing data 41a generated by the given processing of the programs A 12a to C 12c is stored in the post-processing data storage region 40 in a state where the process ID 45 is allocated to the post-processing data 41a. Referring to FIG. 18, post-processing data 411 whose process ID 451 is "12" shows a state in which the pre-processing data L 33a acquired from the external system 170a is stored as the post-processing data.

A flow of the processing in the computer system 150 configured as described above will be described.

FIG. 20 illustrates a processing flow of the data storage device 90.

In S401, the processing data control unit 121 receives a data acquisition request from the program A 12a, and transmits an acquisition request for data corresponding to the request to the pre-processing data collection unit 15 and the external data collection unit 151.

In S403, the pre-processing data collection unit 15 acquires the pre-processing data (pre-processing data X 31a, pre-processing data L 33a, pre-processing data Q 35a) corresponding to the acquisition request from the pre-processing data recording region 30, and the external data collection unit 151 acquires such pre-processing data from the external systems 170a and 170b.

In S405, the data conversion unit 152 calls the conversion programs corresponding to the respective data formats from the conversion program group 155, for the pre-processing data L 33a acquired from the external system 170a, with reference to the conversion rule management table 154, and converts the data format into a data format available in the program A 12a.

In S407, the pre-processing data collection unit 15 transmits the pre-processing data (pre-processing data 31a, etc.) acquired from the pre-processing data storage region 30 to the process ID allocation unit 14, and the data conversion unit 152 transmits the pre-processing data subjected to the data format conversion (pre-processing data L 33a) to the process ID allocation unit 14.

In S409, the process ID allocation unit 16 extracts the maximum value (latest) process ID with reference to the process ID management table 17, increments the process ID by one ("1" if no process ID is recorded), and generates the new process ID.

In S411, the process ID holding unit 13 additionally records the new process ID and the program name of the data acquisition request source to an end of the process ID management table 17 as a new entry in association with each other.

In S413, the process ID allocation unit 16 allocates the new process ID to the pre-processing data, and transmits the pre-processing data to the request source through the processing data control unit 121.

In S415, the process ID allocation unit 16 checks whether subsequent acquisition data is present, or not, and if the data is present (yes in S415), the flow returns to the processing in S409, and if no data is present (no in S415), the flow completes the processing.

In S417, the processing data control unit 121 receives the post-processing data 41a added with the process ID 45a generated by the given processing such as the program A 12a, and enables the post-processing data X 41a in the post-processing data storage region 40.

A flow of the processing of the data recording device 90 in the computer system 150 is described above.

Thereafter, as in the other embodiments, the post-processing data 41 generated from the pre-processing data 31 having the consistency in the program A 12a is provided to the search request source by the data management device 80.

As described above, according to the computer system 150 of the fourth embodiment, also in the configuration using the data of the external system having data of the data format available on the subject computer system, the processing history management such as the data acquisition history can be simply performed with the use of the process ID.

In particular, the data storage device 90 that functions as a shared resource from the program A 12a is provided with a function for consolidating the process ID 45 with the result that there is no need to modify the program A 12a for realizing the management of the processing history. In addition, the processing history management that can deal with the expansion of the external system 170a flexibly and simply can be simply provided.

Fifth Embodiment

In the computer system 150 according to the fourth embodiment, the data storage device 90 collects the pre-processing data from the external system 170a at an opportunity that the execution computer 70a (including the program A 12a) starts the data acquisition event (data acquisition request).

In this situation, if the data storage device 90 acquires the data from the external system 170a in advance before the data acquisition event is issued from the execution computer 70a, an access performance (for example, access speed) to the data required by the execution computer 70a improves. In particular, if the data acquisition of the execution computer 70a is intended for only reference, the convenience and the reduction effects of the load in the system are improved.

However, when the pre-processing data of the data storage device 90 is updated after the pre-processing data has been transmitted to the execution computer 70a according to the data acquisition request such as the execution computer 70a, there arises such a problem that the consistency between the data acquired by the execution computer 70a and the update data of the data storage device 90 cannot be ensured. That is, as long as the data is collected at the opportunity that the execution computer 70a starts the processing, the pre-processing data that can be referred at an arbitrary opportunity cannot be updated.

Under the circumstances, in a computer system 200 according to the fifth embodiment, while the update of the pre-processing data in the data storage device 90 is executed at an arbitrary opportunity, a difference from the data acquired according to the data acquisition request such as the execution computer 70a can be also managed.

FIG. 21 illustrates a configuration of the computer system 200. The computer system 200 has one of the features that a data extraction device 210 is newly provided.

The data extraction device 210 collects (crawls) the pre-processing data from the external systems 170a and 170b, for example, at a scheduled arbitrary opportunity, without depending on the data acquisition request from the execution computer 70a.

Also, the data storage device 90 acquires the pre-processing data from the external system 170a which is acquired from the data extraction device 210 in a given schedule in advance at an opportunity of receiving the data acquisition request from the execution computer 70a, and transmits the pre-processing data added with the process ID 45 to the execution computer 70a of the request source. The process ID 45 and the data acquisition request source are managed by the process ID management table 17 as in the other embodiments.

Also, the data storage device 90 manages a data collection schedule from the external system 170a in the data extraction device 210, and instructs the data storage device to perform the data collection processing at a given time.

The configuration of the data extraction device 210 will be described in detail. The data extraction device includes, in a memory 211, a data transmission/reception unit 220, the external data collection unit 151, the data conversion unit 152, the conversion rule holding unit 153, the conversion rule table 154, and the conversion program group 155. Also, the data extraction device has a storage unit 230 which can store data acquired from the external system 170a.

The data transmission/reception unit 220 receives a data collection instruction from the data storage device 90, collects the pre-processing data L 33a from the external system 170a into the external data collection unit 151, converts the collected data into a given data format, and thereafter outputs the converted data to the data storage device 90.

The external data collection unit 151, the data conversion unit 152, the conversion rule holding unit 153, the conversion rule table 154, and the conversion program group 155 conduct the same processing as that in the fourth embodiment. The data conversion unit 152 calls an appropriate conversion program from the conversion program group 155 according to the data format of the pre-processing data collected by the external data collection unit 151 with reference to the conversion rule table 154 held by the conversion rule holding unit 153, and converts the data format into a data format available in the computer system 200. The data converted in the format is appropriately output to the data storage device 90.

The data storage device 90 newly includes a data collection scheduler 205 in a memory 92. The data collection scheduler 205 holds a collection schedule management table 206.

FIG. 22 schematically illustrates the collection schedule management table 206. The collection schedule management table 206 includes respective items of a collection destination 207 for identifying the external system which is a collection destination of the pre-processing data, a collection schedule item 208 for storing the number of transmission of the data collection instruction per unit time (for example, three times per 60 minutes), and a latest collection time 209 that stores a time at which the data collection processing is finally executed. The collection schedule management table 206 is statically set, and is changeable in setting through a management terminal. The data collection scheduler 205 appropriately transmits a data collection instruction to the data extraction device 210 with reference to the collection schedule management table 206.

The pre-processing data transmitted from the data extraction device 210 according to the data collection instruction is stored in the pre-processing data storage region 30.

A flow of processing in the computer system 200 configured as described above will be described.

FIG. 23 illustrates a processing flow of the data extraction device 210.

In S501, the data transmission/reception unit 220 receives an instruction for pre-processing data collection (crawl) from the data collection scheduler 205 in the data storage device 90, and transmits a data collection command to the external data collection unit 151.

In S503, the external data collection unit 151 collects the pre-processing data from the external systems 170a and 170b, and transmits the pre-processing data to the data conversion unit 152.

In S505, the data conversion unit 152 calls the conversion program corresponding to the data format of the collected data from the conversion program group 155 with reference to the conversion rule table 154 in the data conversion rule holding unit 153, and generates the pre-processing data converted into the data format processable in the computer system 200.

In S507, the data transmission/reception unit 220 transmits the converted pre-processing data to the data storage device 90.

In S509, the processing data control unit 121 receives the post-processing data with the process ID generated by the given processing of the program A 12a, and stores the post-processing data in the post-processing data storage region 40.

A flow of processing in the data extraction device 210 is described above.

FIG. 24 illustrates a processing flow of the data storage device 90.

In S551, the data collection scheduler 205 acquires the collection schedule management table 206.

In S553, the data collection scheduler 205 calculates differences between the latest update time in the respective external systems of the collection schedule management table 206, and the current time.

In S555, the data collector scheduler 205 determines whether the respective external systems having the calculated differential times larger than the corresponding collection schedule are present, or not. If present, the flow proceeds to S557 (yes in S555), and if absent (no in S555), the flow returns to S553, and management of the differential time is continued.

In S557, the processing data control unit 121 transmits a data collection instruction related to the external system whose differential time is larger than the collection schedule to the data transmission/reception unit 220 of the data extraction device 210.

In S559, the processing data control unit 121 waits for the pre-processing data from the external system designated in S557 until the reception from the data extraction device 210 is completed. For example, the processing data control unit 121 waits until, for example, a data transmission completion notification from the data extraction device 210 is received.

In S561, the data collection scheduler 205 receives the data reception completion from the data transmission/reception unit 120, and updates the items of the appropriate external system on the collection schedule management table 206 with the current time as the latest update time.

After the processing in S561, the flow may returns to the leading S551, or the collection scheduler may execute this processing at intervals shorter than the shortest interval.

A flow of the collection schedule processing in the data recording device 90 is described above.

As in the first to fourth embodiments, the pre-processing data L 33a and Q 35a that have been subjected to the data format conversion which are collected in the pre-processing data storage region 30 of the data storage device 90 are appropriately used according to the data acquisition request of the program A 12a, and the processing history management is further conducted on the basis of the process ID 45.

According to the computer system 200 of the fifth embodiment, the data is extracted asynchronously with the processing of the execution computer 70 (program A 12a, etc.). As a result, in addition to the advantages described in the first to fifth embodiments, there is obtained an advantage that all of the Pre-processing data that can be collected from the plural external systems 170a and 170b is stored in the single data storage device 90 to enable reference.

Further, the pre-processing data stored in the data storage device 90 can be updated at an arbitrary opportunity regardless of the opportunity when the execution computer 70a (program A 12a) gives an request for collecting the pre-processing data stored in the data storage device 90.

Sixth Embodiment

A program that performs various kinds of processing can be applied to the program A 12a virtualized in the computer system of the first to fifth embodiments. Among the programs, there is a program that performs processing for generating valuable data by combination of a process frequently using computing resources with high costs or valuable data. In this way, the costs or the values required in a generating process may be different in each of the post-processing data 41a.

In a sixth embodiment, a description will be given of a computer system 250 in which a relevance between the process ID 45 and information (for example, data price) defining the value of the data is further defined to further provide the data value for each of the post-processing data 41

FIG. 25 illustrates a configuration of the computer system 250. The computer system 250 is based on the computer system 1 of the first embodiment. Differences therebetween reside in that a processing cost management table 251 is provided, and a processing history management unit 260 that calculates a data prices on the basis of the processing cost management table 251 for the search result responding to the search request from the search request source, and a search result 270 that outputs the data price calculated to the search request source before providing the search result to the search request source are provided.

FIG. 26 schematically illustrates the processing cost management table 251. The processing cost management table 251 is information that defines the prices of data for each of the programs A 12a to C 12c that generates the post-processing data 41 by the given processing. The processing cost management table 251 is defined by a manager of the computer system 250 in advance. The definition can be appropriately changed in setting.

The processing cost management table 251 includes a program name item 252, and a post-processing data price item 253. In the program name item 252, program names that generate the data 41 are registered. In the data price item 253, data prices per unit amount is registered in each of the programs A 12a to C 12c. The unit amount can be set with a data size or the number of files, and fixed amounts or free can be also set in the unit amount (in the figure, "free" indicates free).

In the processing history management unit 260, as in the first embodiment, the post-processing data group management table 251 is created for the post-processing data 41 collected from the post-processing data storage region 40, and the post-processing data 41 generated from the pre-processing data 31 having the consistency is extracted (refer to FIG. 8). Thereafter, in the processing history management unit 260, the data prices corresponding to the type of the programs are calculated with respect to the extracted post-processing data group on the basis of the processing cost management table 251. The calculated data prices and the post-processing data 41 are transmitted to the search result transmission unit 270.

In the search result transmission unit 270, the prices of the post-processing data 41 is checked. Specifically, data of the program group is checked, and if free, the post-processing data 41 corresponding to the process ID 45 belonging to the group is transmitted to the search request source. If paid, the post-processing data 41 corresponding to the process ID 45 belonging to the group is not transmitted, but instead, the information on the data price is output to the search request source.

FIG. 27 schematically illustrates a search result screen 300 displayed on a screen of the search request source. The search result screen 300 includes a search key input column 305 where the search request source enters the search condition (showing a state where keywords such as "stock price", "rising", and "stocks" are entered), a free search result display column 310 where the search result of the program B 12b whose data price is set to free (free) is displayed, and a paid search result display column 330 where the number of hits and the prices of the programs A 12a and C 12c whose data prices are set to paid are displayed.

In the paid search, at an opportunity when a purchase buttons 331a and 331b are operated by a searcher, (after settlement is conducted through a given payment machine (not shown), the post-processing data 41 corresponding to the respective programs is transmitted from the search result transmission 270, and displayed.

A flow of processing in the data management unit 20 configured as described above will be described.

FIG. 28 illustrates a processing flow of the data management unit 20.

In S601, the post-processing data collection unit 22 collects the post-processing data 41 matching the condition from the post-processing data storage region 40 together with the attendant process ID, in response to the search request input to the search condition reception unit 21 through the input/output device 5.

In S603, the processing history management unit 260 groups the post-processing data 41 for each of the programs A 12*a* to C 12*c* that have executed the processing for management with reference to the process ID management table 17, and extracts the latest (maximum) process ID 45 for each of the groups.

In S605, the processing history management unit 260 acquires the oldest (minimum value) process ID in the respective groups among the latest process ID 45 extracted in each of the groups, as the all-processing completion ID 55.

In S607, the processing history management unit 260 removes the process ID 45 newer (larger) than the all-processing completion ID 55 from the collection data, records the result in the ID list item after removal of an intermediate state 52, and transmits the results to the search result transmission unit 22.

In S609, the processing history management unit 260 calculates the data price for each of the groups with reference to the processing cost management table 251. Specifically, the processing history management unit 260 obtains the data prices for each of the groups for the post-processing data 41 having the process ID 45 belonging to the ID list item after removal of an intermediate state 52 in the post-processing data group management table 24.

In S611, the processing history management unit 260 checks whether the each group is paid or free, and if free, the processing history management unit 260 notifies the search result transmission unit 270 of the free groups. The search result transmission unit 270 transmits the post-processing data 41 in the free groups that have received the notification, corresponding to the process ID recorded in the ID list item after removal of an intermediate state 52 to the search request source (S619).

In S613, the processing history management unit 260 transmits the price data indicative of the prices of data for the paid groups to the search result transmission unit 270.

In S615, the search result transmission unit 270 determines whether the purchase request of the post-processing data of the paid program is received from the search request source, or not, and if the search result transmission unit 270 receives the purchase request, the search result transmission unit 270 transmits the post-processing data 41 of the process ID 45 belonging to the ID list item after removal of an intermediate state 52 in the groups of the paid programs to be purchased to the search request source.

A flow of processing in the data management unit 20 is described above.

According to the computer system 250 of the sixth embodiment, the pre-processing data can be set to prices for each of the processing histories according to the price management of the post-processing data.

The respective embodiments of the present invention have been described above. However, the present invention is not limited to those embodiments, but includes various modified examples without departing from the drift of the present invention. For example, a part of one configuration example can be replaced with another configuration example, and the configuration of one embodiment can be added with the configuration of another embodiment.

Also, parts or all of the above-described respective configurations, functions, processors, may be realized by hardware, for example, by designing an integrated circuit.

The information on the program, table, and file for realizing the respective embodiments can be stored in a magnetic or electronic recording medium.

REFERENCE SIGN LIST

1, 60, 100, 150, 200, 250; computer system
10; data processing unit
13; process ID holding unit
14; process ID allocation unit
17; process ID management table
20; data management unit
30; pre-processing data storage region
31; pre-processing data
40; post-processing data storage region
41; post-processing data
45; process ID
70; execution computer
80; data management device
90; data recording device
117; multistage process ID management table
151; external data collection unit
152; data conversion unit
153; conversion rule holding unit
154; conversion rule table
251; processing cost management table

The invention claimed is:

1. A computer system, comprising:
a computer coupled to a storage device, a communication interface, and a non-transitory computer readable medium storing instructions, that when executed by the computer, cause the computer to:
execute a plurality of processing units that each acquire pre-processing data, each execute given processing on the pre-processing data, and each generate post-processing data as a result of the processing;
newly allocate a respective process identifier (ID) from among a plurality of process IDs for one of the plurality of processing units each time the one of the plurality of processing units is to acquire the pre-processing data, wherein the process IDs collectively indicate an order of acquisition of the pre-processing data by the plurality of processing units;
manage a process management ID table that includes information of the processing units in correspondence with the process IDs which have been allocated to the processing units when the pre-processing data has been acquired by the processing units, the process management ID table being managed in ascending order of the process IDs;
store the post-processing data generated by the processing of each of the plurality of processing units in the storage device in association with the corresponding allocated process IDs;

determine the post-processing data that satisfies a received data search condition from a search request source; and extract the post-processing data associated with a same or earlier process ID than a first process ID that is earliest among the respective latest allocated processing IDs of the plurality of the processing units from the determined post-processing data that satisfies the data search condition, and output the extracted post-processing data to the search request source.

2. The computer system according to claim 1,
wherein the process IDs are information indicating respective times at which the processing units acquire the pre-processing data.

3. The computer system according to claim 1,
wherein the process IDs are managed in association with identification information of the plurality of processing units that acquire the pre-processing data.

4. The computer system according to claim 1,
wherein the non-transitory computer readable medium further stores instructions, that when executed by the computer, cause the computer to:
store dependency information indicating a dependency of the plurality of processing units, and
extract the post-processing data having a same or earlier process ID than a second process ID that is earliest among the respective latest allocated processing IDs of the processing units having the dependency from the post-processing data that satisfies the data search condition.

5. The computer system according to claim 1,
wherein the non-transitory computer readable medium further stores instructions, that when executed by the computer, cause the computer to:
store value management information that defines information indicative of a value of each of the generated post-processing data for each of the plurality of processing units, and
generate value information of the extracted post-processing data with reference to the value management information, output the extracted post-processing data when the value of the extracted post-processing data is a predetermined value or smaller to the search request source, and output the generated value information to the search request source when the value of the extracted post-processing data is larger than the predetermined value.

6. The computer system according to claim 5,
wherein the non-transitory computer readable medium further stores instructions, that when executed by the computer, cause the computer to:
receive a request for acquiring the extracted post-processing data from the search request source after outputting the generated value information, and transmit the extracted post-processing data corresponding to the generated value information to the search request source.

7. The computer system according to claim 5,
wherein the value of each of the generated post-processing data defined by the value management information is a price per unit data amount.

8. The computer system according to claim 6,
wherein the value of each of the generated post-processing data defined by the value management information is a price per unit data amount.

9. The computer system according to claim 1, further comprising:

a data storage computer, coupled to the computer, having a storage unit that stores the pre-processing data acquired by the plurality of processing units,
wherein the storage unit includes an external data acquisition unit that acquires the pre-processing data stored in an external computer connected thereto through a communication line, and stores the acquired pre-processing data in the storage unit when the plurality of processing units request to acquire the pre-processing data.

10. The computer system according to claim 9,
wherein the data storage computer further includes a data format conversion unit that converts the pre-processing data acquired from the external computer into a another data format.

11. The computer system according to claim 10, wherein the non-transitory computer readable medium further stores instructions, that when executed by the computer, cause the computer to:
store data acquisition schedule information in which timings at which the plurality of processing units acquire the pre-processing data stored in the storage unit of the data storage computer is defined for each of the processing units, and
acquire the pre-processing data on the basis of the data acquisition schedule information.

12. A data management method for a computer system including a plurality of processing units that each acquire pre-processing data, each execute a given processing on the pre-processing data, and each generate post-processing data as a result of the processing, and transmit a search result in response to a request for searching the post-processing data, the method comprising:
newly allocating a respective process identifier (ID) from among a plurality of process IDs for one of the plurality of processing units each time the one of the plurality of processing units is to acquire the pre-processing data, wherein the process IDs collectively indicate an order of acquisition of the pre-processing data by the plurality of processing units;
managing a process management ID table that includes information of the processing units in correspondence with the process IDs which have been allocated to the processing units when the pre-processing data has been acquired by the processing units, the process management ID table being managed in ascending order of the process IDs;
storing the post-processing data generated by the processing of each of the processing units in a storage device in association with the corresponding allocated process IDs;
determining the post-processing data that satisfies a received data search condition from a search request source; and
extracting the post-processing data associated with a same or earlier process ID than a first process ID that is earliest among the respective latest allocated processing IDs of the plurality of the processing units from the determined post-processing data that satisfies the search condition, and outputting the extracted post-processing data to the search request source.

13. A non-transitory computer readable recording medium storing a program for causing a computer system having a plurality of processing units to each execute processing to acquire pre-processing data, each execute a given processing on the pre-processing data, and each generate post-processing data as a result of the processing, the program further causing the computer system to:
- newly allocate a respective process identifier (ID) from among a plurality of process IDs for one of the plurality of processing units each time the one of the plurality of processing units is to acquire the pre-processing data, wherein the process IDs collectively indicate an order of acquisition of the pre-processing data by the plurality of processing units;
- manage a process management ID table that includes information of the processing units in correspondence with the process IDs which have been allocated to the processing units when the pre-processing data has been acquired by the processing units, the process management ID table being managed in ascending order of the process IDs;
- store the post-processing data generated by the processing of each of the plurality of processing units in the storage device in association with the corresponding allocated process IDs;
- determine the post-processing data that satisfies a received data search condition from a search request source; and
- extract the post-processing data associated with a same or earlier process ID than a first process ID that is earliest among the respective latest allocated processing IDs of the plurality of the processing units from the determined post-processing data that satisfies the data search condition, and output the extracted post-processing data to the search request source.

* * * * *